(12) United States Patent
Numata et al.

(10) Patent No.: US 8,318,684 B2
(45) Date of Patent: Nov. 27, 2012

(54) ANTIBIOTICS, BISPOLIDES A1, A2, AND A3 AS WELL AS BISPOLIDES B1, B2A, B2B AND B3 AND PROCESSES FOR PRODUCING SAID ANTIBIOTICS

(75) Inventors: Keiichi Numata, Tokyo (JP); Noriyuki Okujo, Tokyo (JP); Siew Eim Khor, Selangor (MY); Lee Li Tan, Selangor (MY); Annie George, Selangor (MY); Szu Ting Ng, Selangor (MY); Chin Jye Tan, Selangor (MY); Hironobu Iinuma, Tokyo (JP); Yasuo Fukagawa, Tokyo (JP); Kunimoto Hotta, Tokyo (JP); Seiji Shibahara, Tokyo (JP); Shinichi Kondo, Tokyo (JP); Satoshi Nimura, Tokyo (JP)

(73) Assignees: Nimura Genetic Solutions Co., Ltd., Tokyo (JP); Forest Research Institute Malaysia, Selangor (MY)

( * ) Notice: Subject to any disclaimer, the term of this patent is extended or adjusted under 35 U.S.C. 154(b) by 522 days.

(21) Appl. No.: 12/300,468

(22) PCT Filed: May 15, 2007

(86) PCT No.: PCT/JP2007/060304
§ 371 (c)(1),
(2), (4) Date: Nov. 10, 2009

(87) PCT Pub. No.: WO2007/132937
PCT Pub. Date: Nov. 22, 2007

(65) Prior Publication Data
US 2010/0144658 A1    Jun. 10, 2010

(30) Foreign Application Priority Data
May 16, 2006   (MY) ............... PI 20062247
Dec. 6, 2006   (MY) ............... PI 20064628

(51) Int. Cl.
*A61K 31/70* (2006.01)
*C07H 17/08* (2006.01)
*C12P 19/62* (2006.01)

(52) U.S. Cl. ............. 514/28; 435/76; 536/7.1; 536/16.8

(58) Field of Classification Search ................... 536/16.8
See application file for complete search history.

(56) References Cited

FOREIGN PATENT DOCUMENTS
JP          11-113588       4/1999

OTHER PUBLICATIONS

Kiyota Keiichi, "Shinki Kosei Busshitsu Bispolide no Hakken ni Tsuite" May 15, 2006,[retrieval date: Jun. 1, 2007], Internet <URL: http://www.ngs-lab.com/news/pdf/JbispolideNews060515.pdf.

Igaraski et al, "Glucosylquestiomycin, a novel antibiotic from *Microbispora* sp. TP-A0184: fermentation, isolation, structure, determination, synthesis and biological activities", pp. 915-920, 1998, vol. 51, No. 10, The Journal of Antibiotics.

Nakajima et al, "*Microbispora coralline* sp. Nov., a new species of genus *Microbispora* isolated from Thai soil", pp. 1761-1767, 1999, vol. 49, No. 4, International Journal of Systematic Bacteriology.

Okujo et al, "Bispolides, novel 20-membered ring macrodiolide antibiotics from *Microbispora*", pp. 216-219, Mar. 25, 2007, vol. 60, No. 3, The Journal of Antibiotics.

*Primary Examiner* — Elli Peselev
(74) *Attorney, Agent, or Firm* — B. Aaron Schulman, Esq.; Stites & Harbison, PLLC

(57) ABSTRACT

Seven novel antibiotic substances can be produced by cultivation of a microbial strain which has been isolated from a soil sample and which is designated as *Microbispora* sp. A 34030 (deposited under an access number FERM BP-10505 in terms of Budapest Treaty). These seven antibiotic substances are named as bispolide A1, bispolide A2, bispolide A3, bispolide B1, bispolide B2a, bispolide B2b and bispolide B3, respectively. These bispolides are each novel compounds which have a chemical structure as collectively represented by the general formula (III) shown below:

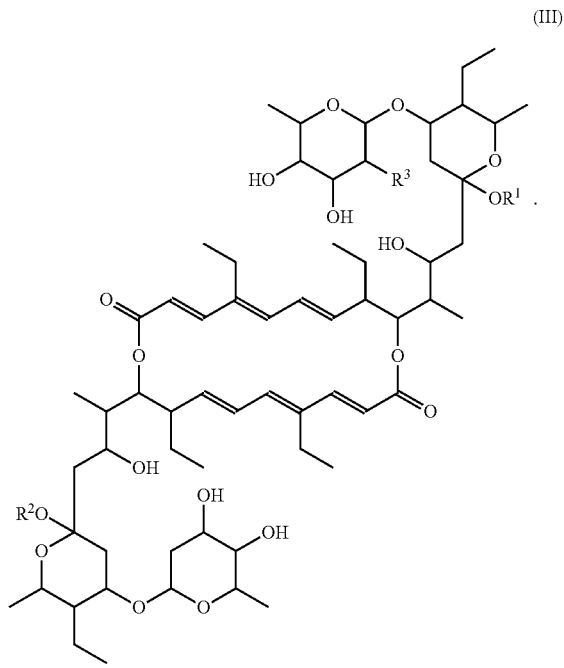

These bispolides have each a high antibacterial activity against a variety of bacteria, particularly Gram-positive bacteria and their antibiotic-resistant strains, and hence these bispolides each are effective and useful for therapeutically treating bacterial infections of Gram-positive bacteria in humans and animals.

14 Claims, 21 Drawing Sheets

FIG. 11

ANTIBIOTICS, BISPOLIDES A1, A2, AND A3 AS WELL AS BISPOLIDES B1, B2A, B2B AND B3 AND PROCESSES FOR PRODUCING SAID ANTIBIOTICS

Novel antibiotics, bispolides A1, A2 and A3, as well as bispolides B1, B2a, B2b and B3, and processes for producing these antibiotics.

CROSS-REFERENCE TO RELATED APPLICATIONS

This application is a US national stage filing under 35 U.S.C. §371 of PCT/JP2007/060304 filed May 15, 2007.

TECHNICAL FIELD

This invention relates to new antibiotics, namely bispolide A1, bispolide A2 and bispolide A3, as well as bispolide B1, bispolide B2a, bispolide B2b and bispolide B3 which each have excellent antibacterial activities.

In this specification, bispolides A1, A2 and A3 may sometimes be designated as a bispolide A collectively, and also bispolides B1, B2a, B2b and B3 may sometimes be designated as a bispolide B collectively.

This invention also relates to a process for producing such a bispolide A, as well as a process for producing such a bispolide B.

Further, this invention relates to a pharmaceutical composition, particularly an antibacterial composition, which comprises such a bispolide A as an active ingredient.

Besides, this invention relates to a pharmaceutical composition, particularly an antibacterial composition, which comprises such a bispolide B as an active ingredient.

Still further, this invention relates to a biologically pure culture of a microbial strain named *Microbispora* sp. A34030, as a new microorganism, which has a characteristic nature that said microbial strain is capable of producing a bispolide A and a bispolide B.

BACKGROUND ART

There are a number of hitherto known antibiotics which are produced by microbials. However, only limited types of the known antibiotics have been used clinically in practice. In the fields of antimicrobial chemotherapy, β-lactam antibiotics such as penicillins and cephalosporins; aminoglycoside antibiotics such as kanamycins; and macrolide antibiotics such as erythromycin have been employed.

While, in the chemotherapy of bacterial infections, the emergence and the increase of antibiotic-resistant bacteria has involved a serious human health problem. Especially, bacterial infection of compromised hosts such as senior citizens and people who have chronic diseases is critical, and thus nosocomial bacterial infections of the inpatients can always invoke a social problem. In the chemotherapy of bacterial infections, the conventional antibiotic drugs do not show an appropriately high antibacterial activity against resistant Gram-positive bacteria such as methicillin-resistant strain of *Staphylococcus aureus* (hereinafter abbreviated as MRSA), vancomycin-resistant *Enterococci* (hereinafter abbreviated as VRE), penicillin-resistant strain of *Streptococcus pneumoniae* (hereinafter abbreviated as PRSP) and β-lactamase negative and ampicillin-resistant *Haemophilus influenzae* (hereinafter abbreviated as BLNAR). Therefore, these antibiotic-resistant bacteria can rise a management problem for the hospitals, that there are emerged nosocomial bacterial infections of patients. For the chemotherapeutic treatment of infection by MRSA, there have been employed arbekacin which is a kanamycin derivative, and vancomycin, but there is remaining a problem that new and more effective antibiotics continue to have been desired to be discovered and provided.

As will be clear from the foregoing situations, there is a keen need for discovery or innovation of new antibiotic therapeutic agent that has new and quite unique chemical structure, an enhanced efficacy, a high specificity and reduced side-effects.

An object of this invention is therefore to provide novel antibiotics which have excellent antibacterial activities and are capable of meeting the requisites as above-mentioned.

On the other hand, it is hitherto known that some microbials can produce 16-membered macrolactone compounds which have a conjugated diene structure along with the hemiacetal moiety and which are called macrobiolides. The known macrobiolides include elaiophylin (see Arcamone, F. M.; Bertazzoli, C.; Ghione, M.; Scotti, T. G; "Microbiol.", Vol. 7, p. 207 (1959) and European patent application publications No. 6297,523A3 and No. 0315,003A3); azalomycin B (see Arai, M; "Antibiot" Ser. A, pp. 13, pp. 46, pp. 51 (1960); and Antibiotic 225 E (see Khlebarova, E. I.; Georgieva-Borisova, I. K.; Sheikova, G. N.; Blinov, N. O; "Farmatsiya (Sofia)" Vol. 22, p. 3 (1972). On the other hand, a known 16-membered macrolactone includes salbomycin (see German Patent application DE 3248280-A, published in 1972), though the structure of salbomycin is identical to that of elaiophylin.

DISCLOSURE OF THE INVENTION

One problem to be solved by this invention is to provide new antibiotics which have excellent antibacterial activities and other meritable properties.

We, the inventors of this invention, have carried out our extensive investigations with our intention of finding out the above-mentioned new and useful antibiotics. As a result, we have now found firstly that a new microbial strain which belongs to the genus *Microbispora* and which has been isolated from a soil sample by us can produce three antibiotics having a novel and common skeletal structure. We have now designated a class of these three antibiotics, as bispolide A1, bispolide A2 and bispolide A3 respectively, which are now collectively named as a bispolide A. We have further found that a bispolide A exhibits strong antibacterial activities against a variety of bacteria such as Gram-positive bacteria as well as their drug-resistant strains.

Thus, the present inventors have now found that the structurally novel and antibacterial three antibiotics which are now designated by the present inventors as bispolide A1, bispolide A2 and bispolide A3 respectively are produced by cultivation of the microbial strain which we have designated as *Microbispora* sp. A34030 and which has been isolated from a soil sample by the present inventors. The present inventors have further found that bispolides A1, A2 and A3 can each exhibit excellent antibacterial activity against Gram-positive bacteria and antibiotic-resistant strains thereof.

Furthermore, the present inventors have continued investigations so as to determine the chemical structures of the above-mentioned three antibiotics which are named as bispolide A1, bispolide A2 and bispolide A3, respectively. Thus, it has now been found and confirmed that these three antibiotic compounds now designated bispolides A1, A2 and A3 respectively have commonly a chemical structure which is represented by the following general formula (I).

(I)

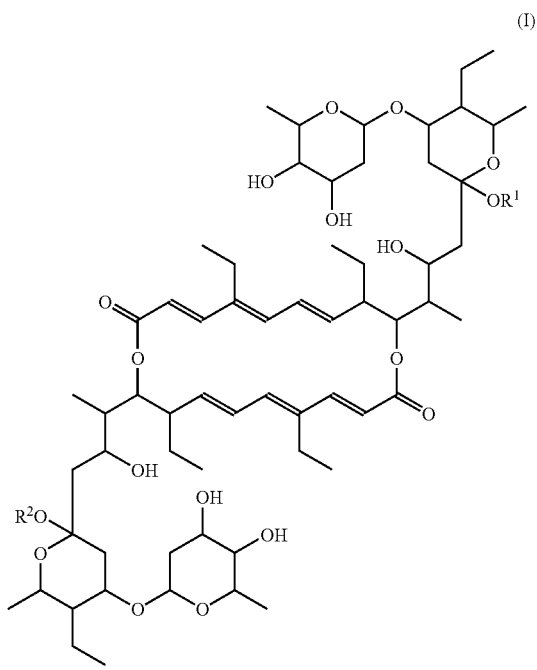

wherein $R^1$ and $R^2$ each denote a hydrogen atom or methyl group (—CH$_3$), and $R^1$ and $R^2$ are each a hydrogen atom for bispolide A1; $R^1$ is a hydrogen atom and $R^2$ is methyl group for bispolide A2; and $R^1$ and $R^2$ are each methyl group for bispolide A3.

As will be clear from the chemical structure of the general formula (I) shown above, bispolides A1, A2 and A3 each contain in the molecule thereof the 20-membered macrolactone ring consisting of symmetric two hydroxyl-carboxylic acids, wherein the respective hydroxyl-carboxylic acid skeleton chain to which the carboxylic carbonyl group is bonded to give a macrolactone ring, has a conjugated α, β-, γ, δ-, ε, ζ-trienic structure.

Further characteristic feature of the chemical structure of a bispolide A is that a cyclic hemiacetal structure or moiety is present in the branch portion or side-chain attached to each of the hydroxyl-carboxylic acid skeleton moieties.

Further, upon a comparison with the aforesaid known 16-membered macrolactones, each compound of bispolides A1, A2 and A3, namely a bispolide A according to this invention is characterized in that the chemical structure of a bispolide A comprises the firstly discovered 20-membered macrolactone structure or moiety which has the conjugated trine portion. Therefore, a bispolide A as mentioned above has a quite new chemical structure unlike the known microbial antibiotic products.

Thereafter, we, the present inventors have continued to make our further investigations and have now discovered that further four new antibiotic substances, which are distinct from said bispolides A1, A2 and A3, are also produced by cultivation of said microbial strain, *Microbispora* sp. A34030.

We, the present inventors, have made further studies to recover these new further four antibiotic substances from the culture of said microbial strain, *Microbispora* sp. A34030 and to isolate these new four antibiotic substances separately from the concurrently produced bispolide A compound of the above-mentioned formula (I) and also from each other. As a result, we have now succeeded in harvesting these new four antibiotic substances, in addition to the aforesaid bispolide A.

Then, the present inventors have designated the thus isolated new four antibiotic substances as bispolide B1, bispolide B2a, bispolide B2b and bispolide B3, respectively.

The present inventors have further found that the newly isolated bispolides B1, B2a, B2b and B3 can exhibit excellent antibacterial activity against various Gram-positive bacteria and antibiotic-resistant strains thereof.

Besides, the present investors have made further investigations, and as an outcome thereof, the present inventors have now found that said new four antibiotics now designated as bispolides B1, B2a, B2b and B3, respectively, contain a common skeleton structure equal to that of the bispolide A and have a chemical structure which is represented by the following general formula (II):

(II)

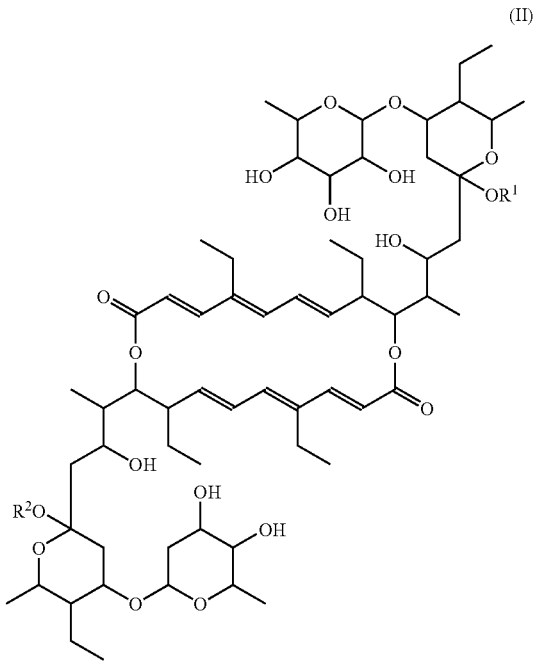

wherein $R^1$ and $R^2$ each denote a hydrogen atom or methyl group (—CH$_3$), and $R^1$ and $R^2$ are each a hydrogen atom for bispolide B1; $R^1$ is a hydrogen atom and $R^2$ is methyl group for bispolide B2a; $R^1$ is methyl group and $R^2$ is a hydrogen atom for bispolide B2b; and $R^1$ and $R^2$ are each a methyl group for bispolide B3.

As will be clear from the general formula (II) shown above, said bispolides B1, B2a, B2b and B3, which may collectively be named as a bispolide B, each contain in the molecule thereof a moiety of the 20-membered cyclic macrolactone consisting of symmetric two hydroxyl-carboxylic acids, respectively, wherein the respective hydroxyl-carboxylic acid skeleton chain to which the carboxylic carbonyl group is bonded has a conjugated α, β-, γ, δ-, and ε, ζ-trienic structure, equally to the bispolide A. Further, an entirely novel characteristic feature of the chemical structure of a bispolide B is that a cyclic hemiacetal structure or moiety is present in the branch portion or side-chain attached to each of the hydroxyl-carboxylic acid skeleton moieties, like the bispolide A mentioned hereinbefore. Bispolide B1, B2a, B2b and B3 (sometimes named as a bispolide B collectively) each have the entirely novel and characteristic chemical structures as described in the above, and in this regard, the bispolide B, similarly to the bispolide A, is clearly differentiated from the previously known 16-membered macrolactones mentioned hereinbefore.

Bispolide A1, bispolide A2 and bispolide A3 (these compounds may be designated as a bispolide A collectively), as well as bispolides B1, B2a, B2b and B3 (these compounds can be designated as a bispolide B collectively), which can have now been obtained newly by the present inventors, are novel antibiotic compounds which can collectively be represented by one general formula (III) as given below.

According to a first aspect of this invention, therefore, there is provided, as new and useful antibiotic substance, an antibiotic which is at least one of bispolide A1, bispolide A2, bispolide A3, bispolide B1, bispolide B2a, bispolide B2b and bispolide B3 that are each a compound represented by the following formula (III):

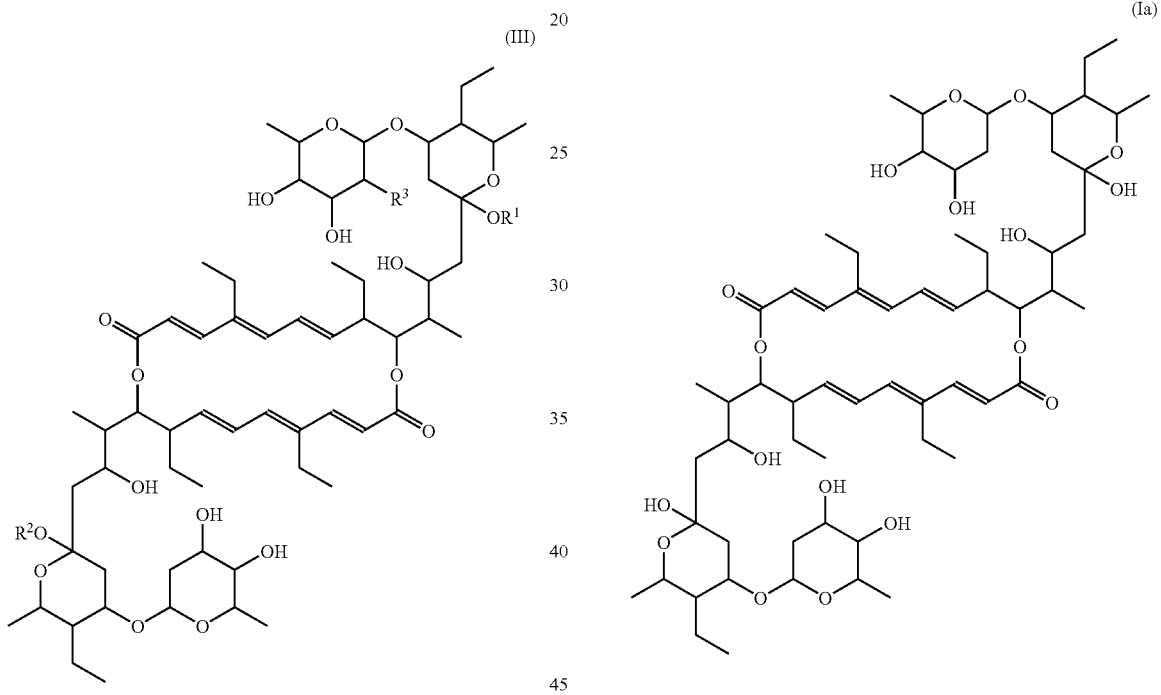

wherein $R^1$ and $R^2$ each denote a hydrogen atom or methyl group and $R^3$ denotes a hydrogen atom or a hydroxyl group, but wherein $R^1$ and $R^2$ are each a hydrogen atom and $R^3$ is a hydrogen atom for bispolide A1; $R^1$ is a hydrogen atom and $R^2$ is methyl group and $R^3$ is a hydrogen atom for bispolide A2; and $R^1$ and $R^2$ are each a methyl group and $R^3$ is a hydrogen atom for bispolide A3, and wherein $R^1$ and $R^2$ are each a hydrogen atom and $R^3$ is hydroxyl group for bispolide B1; $R^1$ is a hydrogen atom, $R^2$ is methyl group and $R^3$ is hydroxyl group for bispolide B2a; $R^1$ is methyl group, $R^2$ is a hydrogen atom and $R^3$ is hydroxyl group for bispolide B2b; and $R^1$ and $R^2$ are each a methyl group and $R^3$ is hydroxyl group for bispolide B3.

In a first embodiment of the first aspect of this invention, there is provided bispolide A1, bispolide A2 or bispolide A3, which is represented by the general formula (I) as given hereinbefore.

Bispolide A1 is the compound of the general formula (I) where $R^1$ and $R^2$ are each a hydrogen atom; bispolide A2 is the compound of the general formula (I) where $R^1$ is a hydrogen atom and $R^2$ is methyl group; and bispolide A3 is the compound of the general formula (I) where $R^1$ and $R^2$ are each a methyl group.

In a second embodiment of the first aspect of this invention, there is provided bispolide B1, bispolide B2a, bispolide B2b or bispolide B3, which is represented by the general formula (II) as given hereinbefore.

Bispolide B1 is the compound of the general formula (II) where $R^1$ and $R^2$ are each a hydrogen atom; bispolide B2a is the compound of the general formula (II) where $R^1$ is a hydrogen atom and $R^2$ is methyl group; bispolide B2b is the compound of the general formula (II) where $R^1$ is methyl group and $R^2$ is a hydrogen atom; and bispolide B3 is the compound of the general formula (II) where $R^1$ and $R^2$ are each a methyl group.

Bispolide A1 has the following formula (Ia):

and the physicochemical properties of bispolide A1 are described below.

(1) Appearance
  Colorless to white colored powder
(2) Molecular Formula

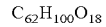

(3) High Resolution Mass Spectrometry (HRFABMS: Anion Mode)
  Found: 1132.1 (M)⁻
  Calculated: 1132.69
(4) Specific Optical Rotation
  $[\alpha]_D^{23}$ +80.0° (c 0.84, in methanol)
(5) Ultraviolet Absorption Spectrum (in Methanol)
  $\lambda_{max}$ (nm) ($\epsilon$): 298 (71,300)
(6) Infrared Absorption Spectrum
  As shown in FIG. 1 of the attached drawings.
(7) Proton Nuclear Magnetic Resonance Spectrum
  Proton NMR spectrum of bispolide A1 as measured in acetone-$d_6$ at 500 MHz at room temperature is shown in FIG. 2 of the attached drawings.

(8) $^{13}$C-Nuclear Magnetic Resonance Spectrum
  $^{13}$C-NMR spectrum of bispolide A1 as measured in acetone-$d_6$ at 125 MHz at room temperature is shown in FIG. 3 of the attached drawings.
(9) Solubility
  Soluble well in methanol, ethanol, dimethylsulfoxide (DMSO), acetone and ethyl acetate, and sparingly soluble in 50% aqueous ethanol (a mixture of ethanol with water at a ratio of 1:1 by volume), but insoluble in water and n-hexane.
(10) TLC
  When bispolide A1 is subjected to a thin layer chromatography on silica gel (Art 1.07734.1000, a product of Merck & Co.) as developed with a solvent system consisting of chloroform-methanol (10:1 by volume), the Rf value is 0.15.
Bispolide A2 has the formula (Ib):

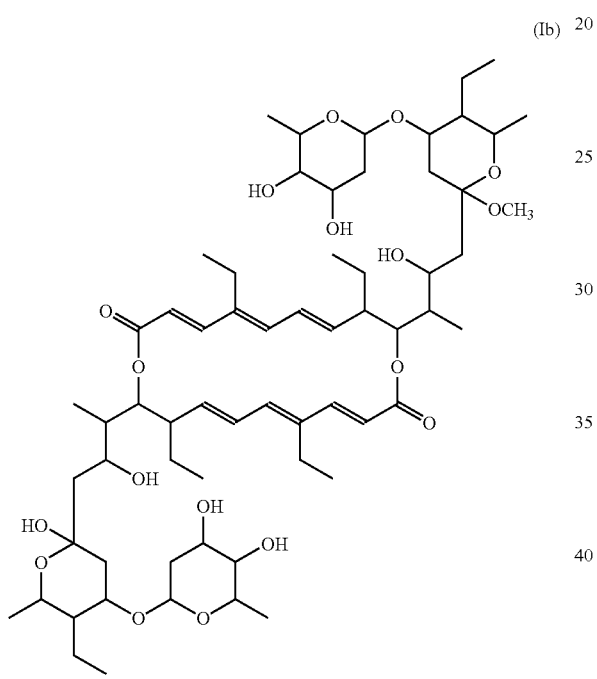

(Ib)

and the physicochemical properties of bispolide A2 are described below.
(1) Appearance
  Colorless to white colored powder
(2) Molecular Formula $C_{63}H_{102}O_{18}$ (3) High Resolution Mass Spectrometry (m/z, FABMS: Anion Mode)
  Found: 1146.1 (M)$^-$
  Calculated: 1146.71
(4) Specific Optical Rotation
  $[\alpha]_D^{23}$ +176.1° (c 0.72, in methanol)
(5) Ultraviolet Absorption Spectrum (in Methanol)
  $\lambda_{max}$ (nm) ($\epsilon$): 298 (90,900)
(6) Infrared Absorption Spectrum
  As shown in FIG. 4 of the attached drawings.
(7) Proton Nuclear Magnetic Resonance Spectrum
  Proton NMR spectrum of bispolide A2 as measured in acetone-$d_6$ at 500 MHz at room temperature is shown in FIG. 5 of the attached drawings.

(8) $^{13}$C-Nuclear Magnetic Resonance Spectrum
  $^{13}$C-NMR spectrum of bispolide A2 as measured in acetone-$d_6$ at 125 MHz at room temperature is shown in FIG. 6 of the attached drawings.
(9) Solubility
  Soluble well in methanol, ethanol, dimethylsulfoxide (DMSO), acetone and ethyl acetate, and sparingly soluble in 50% aqueous ethanol, but insoluble in water and n-hexane.
(10) TLC
  When bispolide A2 is subjected to a thin layer chromatography on silica gel (Art 1.07734.1000, a product of Merck & Co.) as developed with a solvent system consisting of chloroform-methanol (10:1 by volume), the Rf value is 0.23.
Bispolide A3 has the formula (Ic):

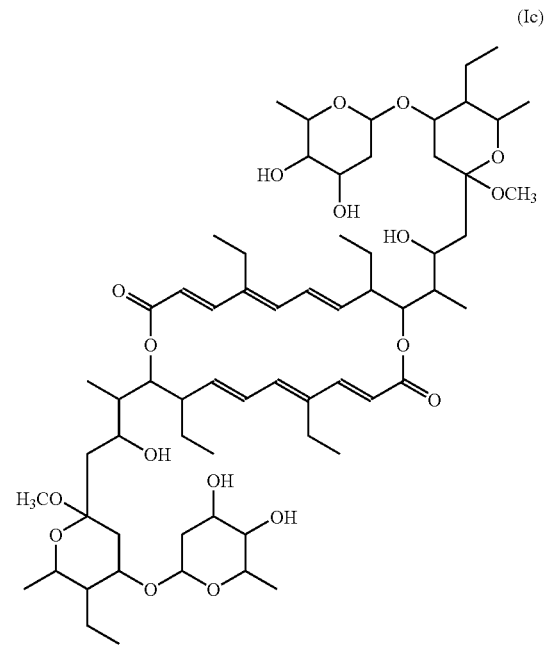

(Ic)

and the physicochemical properties of bispolide A3 described below.
(1) Appearance
  Colorless to white colored powder
(2) Molecular Formula $C_{64}H_{104}O_{18}$ (3) High Resolution Mass Spectrometry (m/z, FABMS: Anion Mode)
  Found: 1160.0 (M)$^-$
  Calculated: 1160.72
(4) Specific Optical Rotation
  $[\alpha]_D^{25}$ +418.7° (c 0.74, in methanol)
(5) Ultraviolet Absorption Spectrum (in Methanol)
  $\lambda_{max}$ (nm) ($\epsilon$): 298 (88,300)
(6) Infrared Absorption Spectrum
  As shown in FIG. 7 of the attached drawings.
(7) Proton Nuclear Magnetic Resonance Spectrum
  Proton NMR spectrum of bispolide A3 as measured in acetone-$d_6$ at 500 MHz at room temperature is shown in FIG. 8 of the attached drawings.

(8) $^{13}$C-Nuclear Magnetic Resonance Spectrum
   $^{13}$C-NMR spectrum of bispolide A3 as measured in acetone-$d_6$ at 125 MHz at room temperature is shown in FIG. 9 of attached drawings.
(9) Solubility
   Soluble well in methanol, ethanol, dimethylsulfoxide (DMSO), acetone and ethyl acetate, and sparingly soluble in 50% aqueous ethanol, but insoluble in water and n-hexane.
(10) TLC
   When bispolide A3 is subjected to a thin layer chromatography on silica gel (Art 1.07734.1000, a product of Merck & Co.) as developed with a solvent system consisting of chloroform-methanol (10:1 by volume), the Rf value is 0.31.

In this specification, bispolide A1 or bispolide A2 or bispolide A3, or any mixture of two or three of these compounds may sometimes be mentioned simply as a bispolide A or a bispolide A compound collectively.

Bispolide B1 mentioned hereinbefore has the following formula (IIa):

(IIa)

and the physicochemical properties of bispolide B1 are described below.
(1) Appearance
   Colorless to white colored powder
(2) Molecular formula $$C_{62}H_{100}O_{19}$$

(3) Mass Spectrometry (FABMS: Anion Mode)
   Found: 1148.9 (M)$^-$
   Calculated: 1148.69
(4) Melting Point
   119.9-121.2° C.
(5) Specific Optical Rotation
   $[\alpha]_D^{23}$+115.0° (c 0.13, in methanol)
(6) Ultraviolet Absorption Spectrum (in Methanol)
   $\lambda_{max}$ (nm) ($\epsilon$): 298 (98,600)
(7) Infrared Absorption Spectrum
   As shown in FIG. 10 of the attached drawings.

(8) Proton Nuclear Magnetic Resonance Spectrum
   Proton NMR spectrum of bispolide B1 as measured in acetone-$d_6$ at 400 MHz at room temperature is shown in FIG. 11 of the attached drawings.
(9) $^{13}$C-Nuclear Magnetic Resonance Spectrum
   $^{13}$C-NMR spectrum of bispolide B1 as measured in acetone-$d_6$ at 100 MHz at room temperature is shown in FIG. 12 of the attached drawings.
(10) Solubility
   Soluble well in methanol, ethanol, dimethylsulfoxide (DMSO), acetone and ethyl acetate, and sparingly soluble in 50% aqueous ethanol (a mixture of ethanol with water at a ratio of 1:1 by volume), but insoluble in water and n-hexane.
(11) TLC
   When bispolide B1 is subjected to a thin layer chromatography on silica gel (Art 1.07734.1000, a product of Merck & Co.) as developed with a solvent system consisting of chloroform-methanol (10:1 by volume), the Rf value is 0.12.

Bispolide B2a mentioned hereinbefore has the following formula (IIb):

(IIB)

and the physicochemical properties of bispolide B2a are described below.
(1) Appearance
   Colorless to white colored powder
(2) Molecular Formula $$C_{63}H_{102}O_{19}$$

(3) Mss Spectrometry (m/z, FABMS: Anion Mode)
   Found: 1162.1 (M)$^-$
   Calculated: 1162.70
(4) Melting Point
   151.5-152.5° C.
(5) Specific Optical Rotation
   $[\alpha]_D^{23}$+103.7° (c 0.15, in methanol)
(6) Ultraviolet Absorption Spectrum (in Methanol)
   $\lambda_{max}$ (nm) ($\epsilon$): 298 (80,500)

(7) Infrared Absorption Spectrum
    As shown in FIG. 13 of the attached drawings.
(8) Proton Nuclear Magnetic Resonance Spectrum
    Proton NMR spectrum of bispolide B2a as measured in acetone-$d_6$ at 400 MHz at room temperature is shown in FIG. 14 of the attached drawings.
(9) $^{13}$C-Nuclear Magnetic Resonance Spectrum
    $^{13}$C-NMR spectrum of bispolide B2a as measured in acetone-4 at 100 MHz at room temperature is shown in FIG. 15 of the attached drawings.
(10) Solubility
    Soluble well in methanol, ethanol, dimethylsulfoxide (DMSO), acetone and ethyl acetate, and sparingly soluble in 50% aqueous ethanol, but insoluble in water and n-hexane.
(11) TLC
    When bispolide B2a is subjected to a thin layer chromatography on silica gel (Art 1.07734.1000, a product of Merck & Co.) as developed with a solvent system consisting of chloroform-methanol (10:1 by volume), the Rf value is 0.16.

Bispolide B2b mentioned hereinbefore has the following formula (IIc):

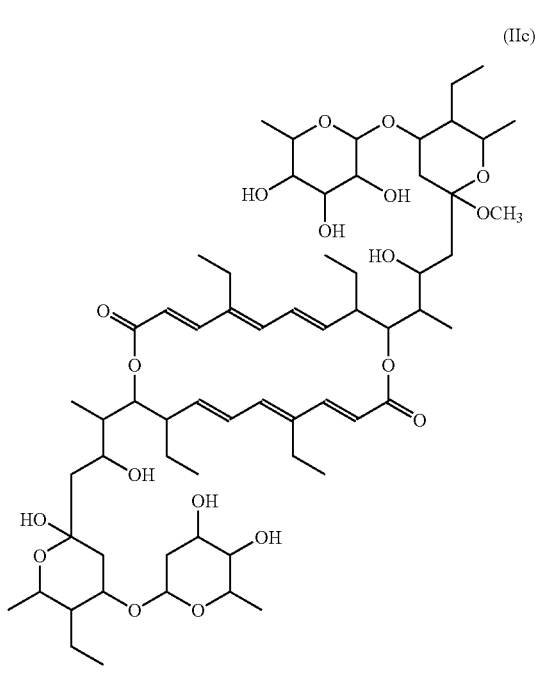

and the physicochemical properties of bispolide B2b are described below.
(1) Appearance
    Colorless to white colored powder
(2) Molecular Formula

$C_{63}H_{102}O_{19}$ (3) Mass Spectrometry (m/z, FABMS: Anion Mode)
    Found: 1162.1 (M)$^-$
    Calculated: 1162.70
(4) Melting Point
    156.2-160.0° C.
(5) Specific Optical Rotation
    $[\alpha]_D^{26}$ +126.3° (c 0.12, in methanol)
(6) Ultraviolet Absorption Spectrum (in Methanol)
    $\lambda_{max}$ (nm) ($\epsilon$): 298 (121,000)

(7) Infrared Absorption Spectrum
    As shown in FIG. 16 of the attached drawings.
(8) Proton Nuclear Magnetic Resonance Spectrum
    Proton NMR spectrum of bispolide B2b as measured in acetone-$d_6$ at 400 MHz at room temperature is shown in FIG. 17 of the attached drawings.
(9) $^{13}$C-Nuclear Magnetic Resonance Spectrum
    $^{13}$C-NMR spectrum of bispolide B2b as measured in acetone-$d_6$ at 100 MHz at room temperature is shown in FIG. 18 of the attached drawings.
(10) Solubility
    Soluble well in methanol, ethanol, dimethylsulfoxide (DMSO), acetone and ethyl acetate, and sparingly soluble in 50% aqueous ethanol, but insoluble in water and n-hexane.
(11) TLC
    When bispolide B2b is subjected to a thin layer chromatography on silica gel (Art 1.07734.1000, a product of Merck & Co.) as developed with a solvent system consisting of chloroform-methanol (10:1 by volume), the Rf value is 0.19.

Bispolide B3 mentioned hereinbefore has the following formula (IId):

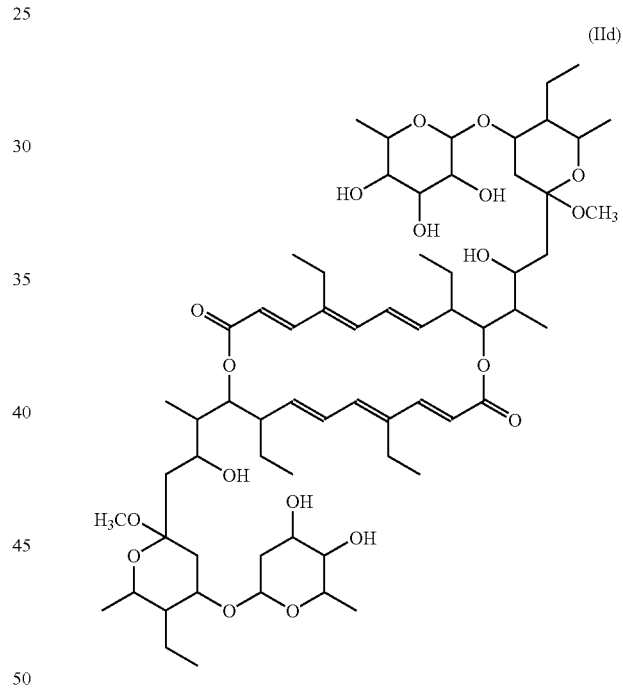

and the physicochemical properties of bispolide B3 are described below.
(1) Appearance
    Colorless to white colored powder
(2) Molecular Formula

$C_{64}H_{104}O_{19}$ (3) Mass Spectrometry (m/z, FABMS: Anion Mode)
    Found: 1176.1 (M)$^-$
    Calculated: 1176.72
(4) Melting Point
    131.5-134.0° C.
(5) Specific Optical Rotation
    $[\alpha]_D^{23}$ +91.7° (c 0.13, in methanol)
(6) Ultraviolet Absorption Spectrum (in Methanol)
    $\lambda_{max}$ (nm) ($\epsilon$): 298 (89,400)

(7) Infrared Absorption Spectrum

As shown in FIG. 19 of the attached drawings.

(8) Proton Nuclear Magnetic Resonance Spectrum

Proton NMR spectrum of bispolide B3 as measured in acetone-$d_6$ at 400 MHz at room temperature is shown in FIG. 20 of the attached drawings.

(9) $^{13}$C-Nuclear Magnetic Resonance Spectrum $^{13}$C-NMR spectrum of bispolide B3 as measured in acetone-$d_6$ at 100 MHz at room temperature is shown in FIG. 21 of attached drawings.

(10) Solubility

Soluble well in methanol, ethanol, dimethylsulfoxide (DMSO), acetone and ethyl acetate, and sparingly soluble in 50% aqueous ethanol, but insoluble in water and n-hexane.

(11) TLC

When bispolide B3 is subjected to a thin layer chromatography on silica gel (Art 1.07734.1000, a product of Merck & Co.) as developed with a solvent system consisting of chloroform-methanol (10:1 by volume), the Rf value is 0.19.

In this specification, bispolide B1 or bispolide B2a or bispolide B2b or bispolide B3, or any mixture of two, three or four of these bispolides B1 to B3 may sometimes be mentioned simply as a bispolide B or a bispolide B compound collectively.

A bispolide A compound having the general formula (I) and a bispolide B compound having the general formula (II) according to this invention have the biological properties hereinafter given.

Thus, bispolide A1, bispolide A2 and bispolide A3 as well as bispolide B1, bispolide B2a, bispolide B2b and bispolide B3 each exhibit excellent antibacterial activities against a variety of Gram-positive bacteria, including their drug-resistant strains (for example, the methicillin-resistant strains). The antibacterial activities of a bispolide A compound and a bispolide B compound are tested by the following procedures.

The antibacterial spectra of a bispolide A compound and a bispolide B compound were tested on a liquid medium consisting of bacto-yeast nitrogen base (a product of Difco Laboratories)-glucose-NZ-amine by a standard serial dilution method. The test results are shown in Table 1 and Table 2 below.

TABLE 1

Antibacterial activities of a bispolide A

| Microorganisms tested | Minimum growth inhibitory concentration (µg/ml) | | |
|---|---|---|---|
| | Bispolide A1 | Bispolide A2 | Bispolide A3 |
| *Bacillus subtilis* PCI 219 | 0.390 | 0.78 | 0.78 |
| *Staphylococcus aureus* FDA209P | 1.560 | 1.56 | 1.56 |
| MRSA ngs1* | 12.50 | 1.56 | 1.56 |
| MRSA ngs2* | ≦0.049 | 3.13 | 3.13 |

*means methicillin-resistant strain of *Staphylococcus aureus*

TABLE 2

Antibacterial activities of a bispolide B

| Microorganisms tested | Minimum growth inhibitory concentration (µg/ml) | | | |
|---|---|---|---|---|
| | bispolide B1 | bispolide B2a | bispolide B2b | bispolide B3 |
| *Bacillus subtilis* PCI 219 | 0.20 | 0.39 | 0.39 | 0.78 |
| *Staphylococcus aureus* FDA209P | 1.56 | 1.56 | 0.78 | 1.56 |
| MRSA ngs1* | 0.39 | 1.56 | 1.56 | 1.56 |
| MRSA ngs2* | ≦0.049 | 1.56 | 3.13 | 3.13 |

*means methicillin-resistant strain of *Staphylococcus aureus*

Further, according to a second aspect of this invention, there is provided a process for the production of the antibiotic, bispolide A1, bispolide A2, bispolide A3, bispolide B1, bispolide B2a, bispolide B2b and/or bispolide B3 having the general formula (III) as defined hereinbefore, which process comprises cultivating a bispolide-producing microbial strain of the genus *Microbispora* that is capable of producing at least one of bispolide A1, bispolide A2, bispolide A3, bispolide B1, bispolide B2a, bispolide B2b and bispolide B3 having the general formula (III) as above, in a culture medium to produce and accumulate at least one of bispolides A1, A2 and A3 as well as bispolides B1, B2a, B2b and B3 in the resulting culture, and recovering at least one of bispolide A1, bispolide A2, bispolide A3, bispolide B1, bispolide B2a, bispolide B2b and bispolide B3 from the resulting culture.

The new microorganism or microbial strain, which is capable of producing the new antibiotics, namely a bispolide A or B compound and is usable in the process according to the second aspect of this invention, may be any strain of those microorganisms which have an ability of producing the said new antibiotics that possess the above-mentioned physico-chemical properties and biological properties, and it can be chosen from a wide variety of microorganisms. Among such usable microorganisms, there may be quoted a strain of the genus *Microbispora* which is designated as *Microbispora* sp. A34030, and which has been isolated by us from a soil sample collected in Sallen Keruing Trail of Forest Research Institute of Malaysia (abbreviated as FRIM) in November of 2002, as one preferred concrete example of the microorganism which is usable in the process of this invention and is capable of producing the desired new antibiotics, bispolide A or B compound.

The above-mentioned strain A34030 of the genus *Microbispora* has been deposited in a Japanese International depository, the International Patent Organism Depositary (abbreviated as IPOD) of the National Institute of Advanced Industrial Science and Technology as located at No. 1-3, Higashi 1-chome, Tsukuba-City, Ibaraki-ken, Japan, under the deposit number of "FERM BP-10505" since Feb. 14, 2006 in terms of the Budapest Treaty.

The microbiological properties of the strain *Microbispora* sp. A34030 are now described below.

1. Morphology

The strain *Microbispora* sp. A34030, on a starch-inorganic salt-agar medium (ISP medium No. 4), has branched substrate mycelia, from which extend relatively long aerial hyphae with the formation of characteristic 2-turned spiral spores at the tips of the aerial hyphae. The motility of the spores was not observed.

2. Growth Characteristics on Various Culture Media
(1) On yeast extract-malt extract—agar medium (ISP-medium No. 2, cultured at 27° C. for 2 weeks), no growth was observed.
(2) On oatmeal agar medium (ISP-medium No 3, cultured at 27° C. for 2 weeks), on inorganic salt-starch agar medium (ISP-medium No. 4, cultured at 27° C. for 2 weeks) and on glycerol-asparagine agar medium (ISP-medium No. 5, cultured at 27° C. for 2 weeks), white to slightly milky white-colored flat colonies were observed.
(3) On a modified Bennett medium (comprising soluble starch 0.5%, glucose 0.5%, meat extract 0.1%, yeast extract 0.1%, NZ-amine 0.2%, NaCl 0.2%, calcium carbonate 0.1%; pH7.0-7.2), the growth was better than on the media mentioned above, while the aerial hyphae were formed only on the outside of the colonies.

3. Physiological Properties
(1) Temperature Range for the Growing
On the modified Bennett medium, the strain A34030 could grow at the temperature range of 20° C. to 37° C. when tested at 10° C., 20° C., 28° C., 30° C., 37° C., 40° C. and 45° C. for 2 weeks. The optimum temperature for growth may be in the vicinity of 28° C. to 30° C.
(2) Hydrolysis of Starch (in an Inorganic Salts-starch Agar Medium, ISP-Medium No. 4, Cultured at 27° C.)
The hydrolysis of starch was not observed for the 2 weeks-cultivation.
(3) Formation of Melanoid Pigment (in Peptone-yeast Extract Iron-Agar Medium, ISP-Medium No. 6; Tyrosine Agar Medium, ISP-Medium No. 7; Cultured at 28° C. in Each Medium)
For the 2 weeks-cultivation at 28° C., formation of melanoid pigment was negative in all the media used.
(4) Utilization of Carbon Sources (in Pridham-Gottlieb Agar Medium, ISP-Medium No. 9, Cultured at 27° C.)
Comparing to the growth of the strain A34030 on a D-glucose-supplemented medium as a positive control, addition of L-arabinose, D-fructose, sucrose, D-xylose and D-mannitol gave a similar growth of the strain A34030, respectively. On the other hand, addition of myo-inositol gave lesser growth of the strain, and on rhamnose-supplemented medium, the growth was not observed. Addition of raffinose gave better growth of the strain A34030 than that of D-glucose.
(5) Reduction of Nitrate (in an Aqueous Peptone Solution Containing 0.1% Potassium Nitrate, ISP-Medium No. 8, Cultured at 28° C.)
The result is not clear, but probably negative.

4. Study of Chemical Composition of the Strain A34030
(1) Meso-2,6-diaminopimelic acid was identified as the major constituent of the cell wall of this strain.
(2) Menaquinone
Predominant menaquinones present in the bacterial cell of this strain were MK-9 and MK($H_2$) at a rate of about 70% to about 30%.
(3) Fatty Acid in the Cell of this Strain
C16:0 ISO (42%), C17:1 w8c (9.8%) and C17:0 10-methyl (9.7%) were determined as the major fatty acid.

5. 16S rDNA Analysis
1239 Bases of the 16S rDNA isolated from the strain A34030 were determined and compared with the hitherto known 16S rDNA of *Streptomyces* which have been deposited on the DNA Data Base. From the above comparison, it was revealed that the 16S rDNA isolated from the strain A34030 has a high homology with that of the genus *Microbispora* belonging to *Streptomyces*.

Summarizing the above-mentioned properties of the strain *Microbispora* sp. A34030, this strain is characterized in that it has branched substrate mycelia and straight aerial hyphae which extend with formation of white to milky white-colored two spirals; that on substrate mycelia, no aerial hyphae was grown; that none of any other characteristic structure was observed; neither soluble pigment is observed on the various tested mediums; nor the formation of melanoid pigment; that the solubilization of starch is not observed; that reduction of nitrate is not decidable, but probably negative.

From the study on the chemical composition of the A34030 strain, it was identified that 2,6-diaminopimelic acid is the cell walls constituent; that MK-9 and MK-9 ($H_2$) are the predominant menaquinone, and that, as the major fatty acid, C16:0 ISO (42%), C17:1 w8c (9.8%) and C17:0 10-methyl (9.7%) were present.

In view of these properties mentioned above, it is presumed that the strain A34030 belongs to the genus *Microbispora* (see Identification Manual of *Actinomycetes*, The Society for *Actinomycete* Japan, 2001, Business Center for Academic Societies Japan), and thus the strain A34030 has been designated as *Microbispora* sp. A34030.

As described hereinbefore, the strain A34030 has been deposited in the aforesaid Japanese international depository "IPOD" of the National Institute of Advanced Industrial Science and Technology, as located at No. 1-3, Higashi 1-chome, Tsukuba-City, Ibaraki-ken, Japan, under the deposit number of "FERM BP-10505" in terms of the Budapest Treaty.

According to the second aspect process of this invention, the production of the antibiotics, bispolides A1, A2 and A3 as well as bispolides B1, B2a, B2b and B3 may be carried out in a manner as described below.

Thus, the production of the aforesaid antibiotic, a bispolide A compound and a bispolide B compound may be carried out by inoculating at first a microbial strain capable of producing a bispolide A compound and/or a bispolide B compound to a nutrient culture medium which comprises the known carbon source, nitrogen source and inorganic salts, and subsequently cultivating the inoculated microbial strain in the culture medium. As the carbon sources, there may be used carbohydrates such as glucose, maltose, molasses, dextrin, glycerin and starch, as well as fats such as soybean oil and peanut oil. As the nutrient sources, there may be used nitrogen sources, for example, peptone, meat extract, cotton seed flour, soybean flour, yeast extract, casein, corn steep liquor, NZ-amine, ammonium sulfate, ammonium nitrate and ammonium chloride.

Further, there may be supplemented to the culture medium inorganic salts such as dipotassium hydrogen orthophosphate, sodium phosphate, sodium chloride, calcium carbonate and magnesium sulfate. If necessary, other additives, for example, a metal such as cobalt and iron may be added in a very small amount. These nutrients present in the culture medium used may be any of those materials which are utilizable by a bispolide A and/or B-producing strain for the production of a bispolide A and/or a bispolide B, and which are known to be utilizable in the conventional culture media for the cultivation of *Actinomycetes*. The aforesaid bispolide A and/or B-producing strain is hereinafter called merely as the bispolide-producing microbial strain.

The proportion of the above-mentioned nutrients in the culture medium are not limited specifically and may be changed greatly, and the best kind of the nutrients and the best proportions of them may be determined according to some preliminary cultivation experiments in a small scale. Nutrient culture medium comprising said nutrients above may be sterilized prior to the inoculation and cultivation of the bispolide-producing microbial strain, and pH of the culture medium may be adjusted properly to a pH of 6 to 8, especially a pH between 6.5 and 7.5, before or after the sterilization of the culture medium.

For the production of the new antibiotic, a bispolide A or a bispolide B compound according to this invention, there may be used any one of general methods for the cultivation of a microorganism which are hitherto known to produce the antibiotics by culturing *Actinomycetes*. It is preferred to carryout the cultivation of the bispolide-producing microbial strain under aerobic condition with agitation and with or without aeration. There may be used a cultivation methods such as static cultivation, shaking cultivation and submerged cultivation in a liquid culture medium with aeration and agitation The submerged cultivation in the liquid culture medium is preferable for the purpose of a large scale production of a bispolide A or a bispolide B.

The cultivation temperature is not specifically limited, so far as it is within the range of temperatures at which the desired antibiotics can be produced without substantially preventing the growth of the bispolide-producing microbial strain as used and innoculated. The cultivation temperature may be chosen depending upon the nature of a bispolide-producing microbial strain as used, and a preferred cultivation temperature may be in a range of 25° C. to 30° C.

The cultivation may be continued until sufficient amount of a bispolide A or B has been produced and accumulated in the resulting culture. The cultivation time is variable depending on the culture medium, cultivation temperature and the microbial strain used. After the cultivation for 72 to 120 hours, bispolides A1 to A3 as well as bispolide B1 to B3 may usually be produced in sufficient amounts.

The potency of a bispolide A or B present in the resulting culture or culture broth as obtained from the cultivation of the bispolide-producing microbial strain employed may be measured by a cylinder plate method in which *Staphylococcus aureus* FDA 209P is used as an assaying strain.

A bispolide A or a bispolide B, generally a bispolide compound as produced and thus accumulated in the resulting culture broth after the cultivation of the bispolide-producing microbial strain may be recovered from the culture broth in a known manner. After the cultivation, the cultured microbial cell body of the microbial strain may firstly be separated from the culture broth by conventional methods such as filtration or centrifugation.

When the cultured microbial cells as produced by the cultivation of the bispolide-producing microbial strain have been separated from the resulting culture broth by filtration or centrifugation, there may be afforded the culture broth filtrate or supernatant which is an aqueous phase. Since the bispolide compounds, including bispolide A1 to A3 and bispolide B1 to B3, are each substantially insoluble in water, the major quantities of bispolides as produced can accumulate and are present in the cultured microbial cell so separated.

For the recovery of the bispolide compound(s) from the cultured microbial cells, it is convenient that the cultured microbial cells as separated is extracted once or twice with a suitable organic solvent such as methanol and ethyl acetate to give an organic extract or extracts containing the bispolide compound(s) dissolved therein. It is also possible that the cultured microbial cells separated as above is firstly disintegrated mechanically, for example, under a ultrasonic wave, to give a homogeneous mixture comprising the whole constituents of the disrupted cells, which is then extracted with a suitable organic solvent such as methanol to give an organic extract containing the bispolide compound(s) dissolved therein. If necessary, it is possible that the above-mentioned culture broth filtrate or supernatant is extracted with a water-immiscible organic solvent such as butyl acetate to give an organic extract containing a second crop of the bispolide compound(s) which was contained in said filtrate or supernatant.

The bispolide compound(s)-containing organic extracts obtained as above may then be combined together and the resulting combined organic extract solution may subsequently be concentrated by evaporation of the organic solvent under a reduced pressure to give a concentrated solution of a smaller volume containing the bispolide compound(s) dissolved therein. This concentrated solution may then be extracted with a suitable organic solvent such as ethyl acetate and butyl acetate, and the resulting extract in the organic solvent used may then be dried over anhydrous sodium sulfate and the resultant dried extract may subsequently be concentrated to dryness under a reduced pressure. The solid residue so produced is a crude product comprising the bispolide compound(s), which may be a crude mixture of bispolides A1, to A3 and/or bispolides B1 to B3 occasionally containing any contaminant(s).

For the purification and isolation of bispolides A1, A2 and A3, as well as bispolides B1, B2a, B2b and B3, it is possible that the aforesaid solid residue comprising the crude product of the bispolide A and the bispolide B is subjected to a chromatographic procedure, a gel-filtration procedure or a countercurrent distribution procedure which may be effected in a conventional way, singly or in combination. For the stationary phase of the conventional chromatographic procedure, for instance, there may be used a known adsorbent such as activated charcoal, silica gel, a micro-porous resin made of a polystyrene-divinyl benzene co-polymer (eg., a commercially available product of a tradename "Diaion HP-20", a product of Mitsubishi Chemical Co., Japan), or a variety of commercially available ion-exchange resins for the chromatographic use.

When the above-mentioned *Microbispora* sp. A34030 strain is employed as said bispolide A or B-producing microbial strain, namely the bispolide-producing microbial strain, the *Microbispora* sp. A34030 upon its cultivation can produce bispolides A1, A2 and A3 concurrently, in addition to bispolides B1, B2a, B2b and B3 as produced. Thus, there can be afforded the resulting culture or culture both containing bispolides A1 to A3 as well as bispolides B1 to B3 so co-produced.

Even when the *Microbispora* sp. A34030 strain is cultured for a main purpose of producing a bispolides A, and also when the *Microbispora* sp. A34030 strain is cultured for a main purpose of producing a bispolide B, this particular A34030 strain may be cultivated in the same way as described above, and the recovery of a bispolide A and the recovery of a bispolide B from the resulting culture or culture broth may be conducted in the same way as described above, since a bispolide A has very similar physicochemical properties to those of a bispolide B. The major quantities of a bispolide A and a bispolide B as co-produced can accumulate and are present in the cultured microbial cells of *Microbispora* sp. A34030 strain which have been separated from the resulting culture or culture broth of said particular strain.

When bispolides A1 to A3, or bispolides B1 to B3 are recovered from the cultured microbial cells of *Microbispora* sp. A34030 by extracting with a suitable organic solvent such as methanol, ethanol and ethyl acetate, there may also be recovered bispolides A1 to A3 and bispolides B1 to B3 concurrently from said cultured microbial cells of *Microbispora* sp. A34030, so that an organic extract or extracts containing a bispolide A and a bispolide B dissolved therein is or are obtained. The organic extract or these organic extracts so obtained may subsequently be treated in the same manner as described above so as to afford a crude mixture comprising bispolides A1, A2 and A3 and also bispolides B1, B2a, B2b and B3 which may occasionally contain any contaminant(s). This crude mixture of the bispolides may then be subjected to a chromatographic procedure same as that described hereinbefore, for the purpose of purifying and isolating each of a bispolide A, particularly each of bispolide A1, bispolide A2 and bispolide A3, as well as each of a bispolide B, particularly each of bispolide B1, bispolide B2a, bispolide B2b and bispolide B3.

In order to isolate bispolides A1, A2 and A3 from each other and possibly also from the bispolide B compound, or in order to isolate bispolides B1, B2a, B2b and B3 from each other and possibly also from the bispolide A compound, it is possible that the crude or partially purified mixture composed of bispolide A1, A2 and A3 as well as bispolides B1, B2a, B2b and B3 is subjected to a high performance liquid chromatography (HPLC) with a suitable stationary phase material and with a suitable development solvent as the mobile phase. In this way, there may be harvested separately an isolated pure product of bispolide A1, an isolated pure product of bispolide A2 and an isolated pure product of bispolide A3, as well as an isolated pure product of bispolide B1, an isolated pure product of bispolide B2a, an isolated pure product of bispolide B2b and an isolated pure product of bispolide B3 which each have the aforesaid physicochemical properties, respectively.

In a particular embodiment of the process according to the second aspect of this invention, therefore, there is provided a process for the production of a bispolide A1 and/or a bispolide B, which process comprises cultivating *Microbispora* sp. A34030 strain (deposited under the deposit number of FERM BP-10505) in a culture medium under aerobic conditions to produce and accumulate bispolide A1, bispolide A2 and bispolide A3 having the general formula (I) as defined hereinbefore, as well as bispolide B1, bispolide B2a, bispolide B2b and bispolide B3 having the general formula (II) as defined hereinbefore, in the resulting culture, and then recovering at least one of bispolide A1, bispolide A2 and bispolide A3 as well as at least one of bispolide B1, bispolide B2a, bispolide B2b and bispolide B3, whereby at least one of bispolides A1, A2 and A3 and at least one of bispolide B1, B2a, B2b and B3 are harvested from said culture.

Further, according to a third aspect of this invention, there is provided a pharmaceutical composition comprising as an active ingredient, at least one of bispolide A1, bispolide A2 and bispolide A3 having the general formula (I) as defined hereinbefore, as well as bispolide B1, bispolide B2a, bispolide B2b and bispolide B3 having the general formula (II) as defined hereinbefore, in admixture with a pharmaceutically acceptable carrier or carriers.

The pharmaceutical composition may particularly be an antibacterial composition according to the third aspect of this invention, and such pharmaceutical composition may be in the form of a preparation or formulation which comprises as the active ingredient a bispolide A compound of the general formula (I) or a bispolide B compound of the general formula (II), in admixture with a conventional, pharmaceutically acceptable solid or liquid carrier, for example, ethanol, water, physiological saline, starch and the like.

A bispolide A compound of the general formula (I) or bispolide B compound of the general formula (II), which is to be used in the pharmaceutical composition according to the third aspect of this invention, may be administered orally or parenterally by intravenous, intramuscular or intraperitoneal administration, and so on.

For the oral administrations, the pharmaceutical composition according to the third aspect of this invention may be formulated in the form of a preparation such as powder, tablets, capsules, suspension, syrup and the like, by blending the active ingredient, namely a bispolide A or bispolide B compound of the general formula (III) with a conventional, pharmaceutically acceptable solid or liquid carrier.

The proportion of the bispolide A or bispolide B compound of the general formula (III) which is incorporated as the active ingredient in the pharmaceutical composition of the third aspect of this invention may depend upon the type of the preparation, but a convenient proportion of the bispolide compound may be in the range of about 2% to 90%, based on the weight of the dosage unit of the composition.

In cases where the composition of the third aspect of this invention is formulated into injections, a preferred form of the injectable preparations may include a sterilized aqueous solution or a sterilized and lyophilized preparation which contains the bispolide A compound of the general formula (I) or the bispolide B compound of the general formula (II) as active ingredient, with or without an appropriate solubilizing agent. For the examples of the liquid carriers usable for this purpose, water, ethanol, aqueous ethanol, glycerol, propylene glycol, vegetable oil and the like are preferred.

The dose of a bispolide A compound of the general formula (I) or a bispolide B compound of the general formula (II) usable as an active ingredient in the composition of this invention may depend upon the nature of bacterial infections to be treated, a purpose of the therapeutic treatment, degree of the patient's conditions and so on. However, an optimal dose of a bispolide A compound or a bispolide B compound can be decided by experts through suitable preliminary tests. By the way, a bispolide A did not exhibit any symptom of toxicity in mice (ICR type, 4 weeks-aged, male), when it was administered intravenously at a dose of 75 mg/kg of a bispolide A. Further, a bispolide B did not exhibit any symptom of toxicity in mice (ICR type, 4 weeks-aged, male), when it was administered intraperitonealy at a dose of 10 mg/kg of a bispolide B.

Further, according to a fourth aspect of this invention, there is provided as a new microorganism, an isolated and biologically pure culture of a microbial strain designated as *Microbispora* sp. A34030 which has a characteristic nature that said microbial strain is capable of producing at least one of bispolide A1, bispolide A2 and bispolide A3 having the general formula (I) defined hereinbefore, as well as at least one of bispolide B1, bispolide B2a, bispolide B2b and bispolide B3 having the general formula (II) defined hereinbefore, and which has been deposited in the International Patent Organism Depositary (abbreviated as "IPOD") of the National Institute of Advanced Industrial Science and Technology in Japan, under the deposit number of FERM BP-10505 in terms of the Budapest Treaty.

BRIEF DESCRIPTION OF THE DRAWINGS

Figure 11:
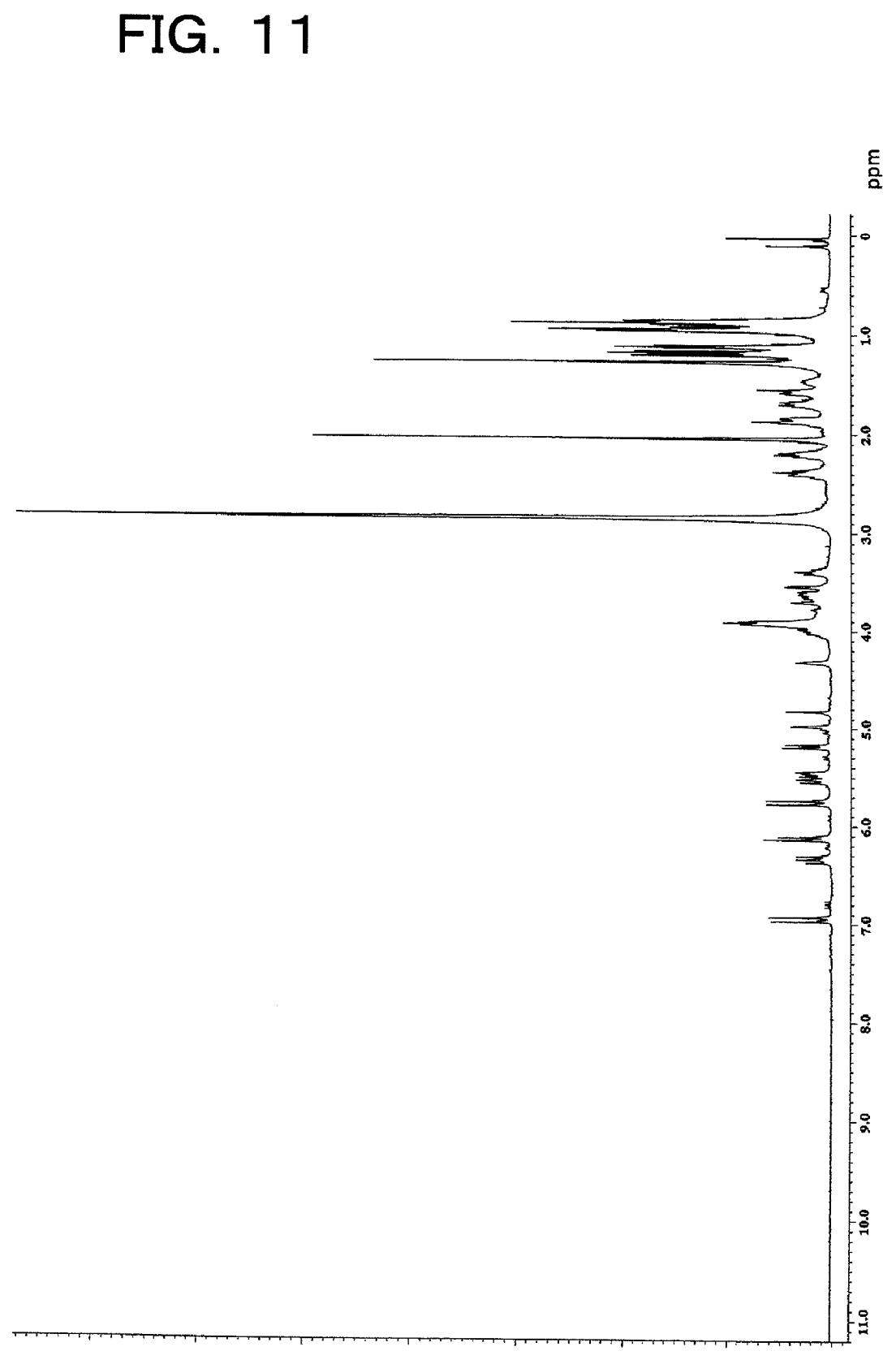

FIG. 11 is proton nuclear magnetic resonance spectrum of bispolide B1 as measured in acetone-$d_6$ solution at 400 MHz at room temperature.

BEST MODE FOR CARRYING OUT THE INVENTION

Figure 1:
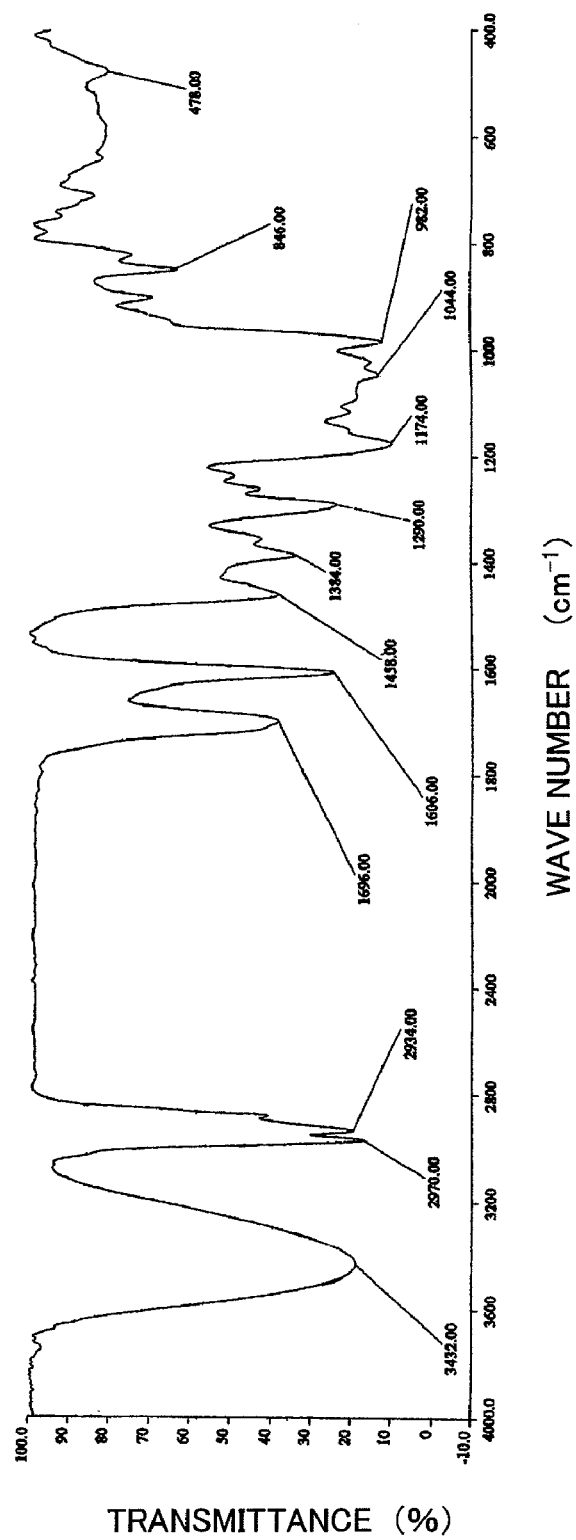
FIG. 1 is infrared absorption spectrum of bispolide A1 as measured by KBr-tableted method.
Figure 2:
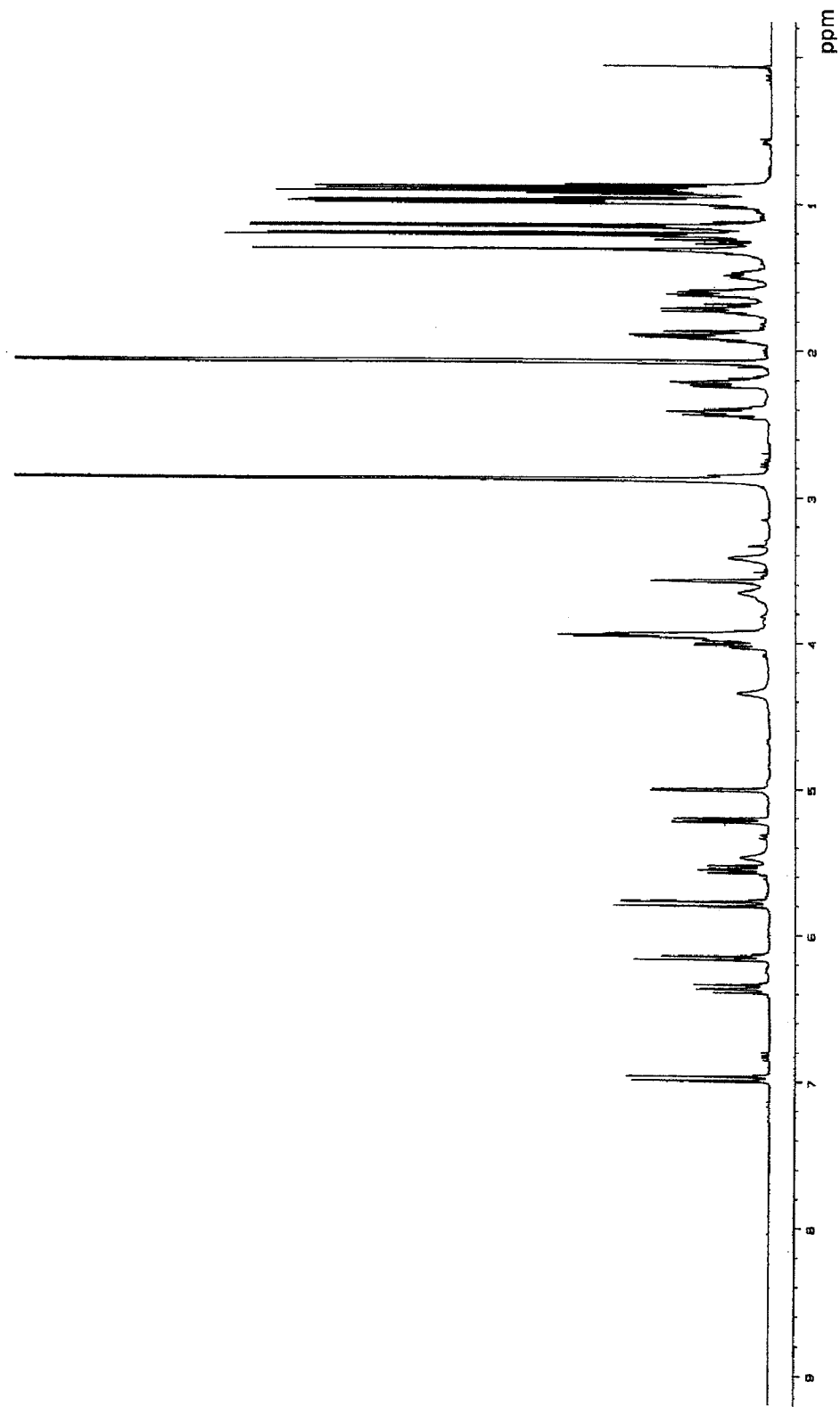
FIG. 2 is proton nuclear magnetic resonance spectrum of bispolide A1 as measured in acetone-$d_6$ solution at 500 MHz at room temperature.
Figure 3:
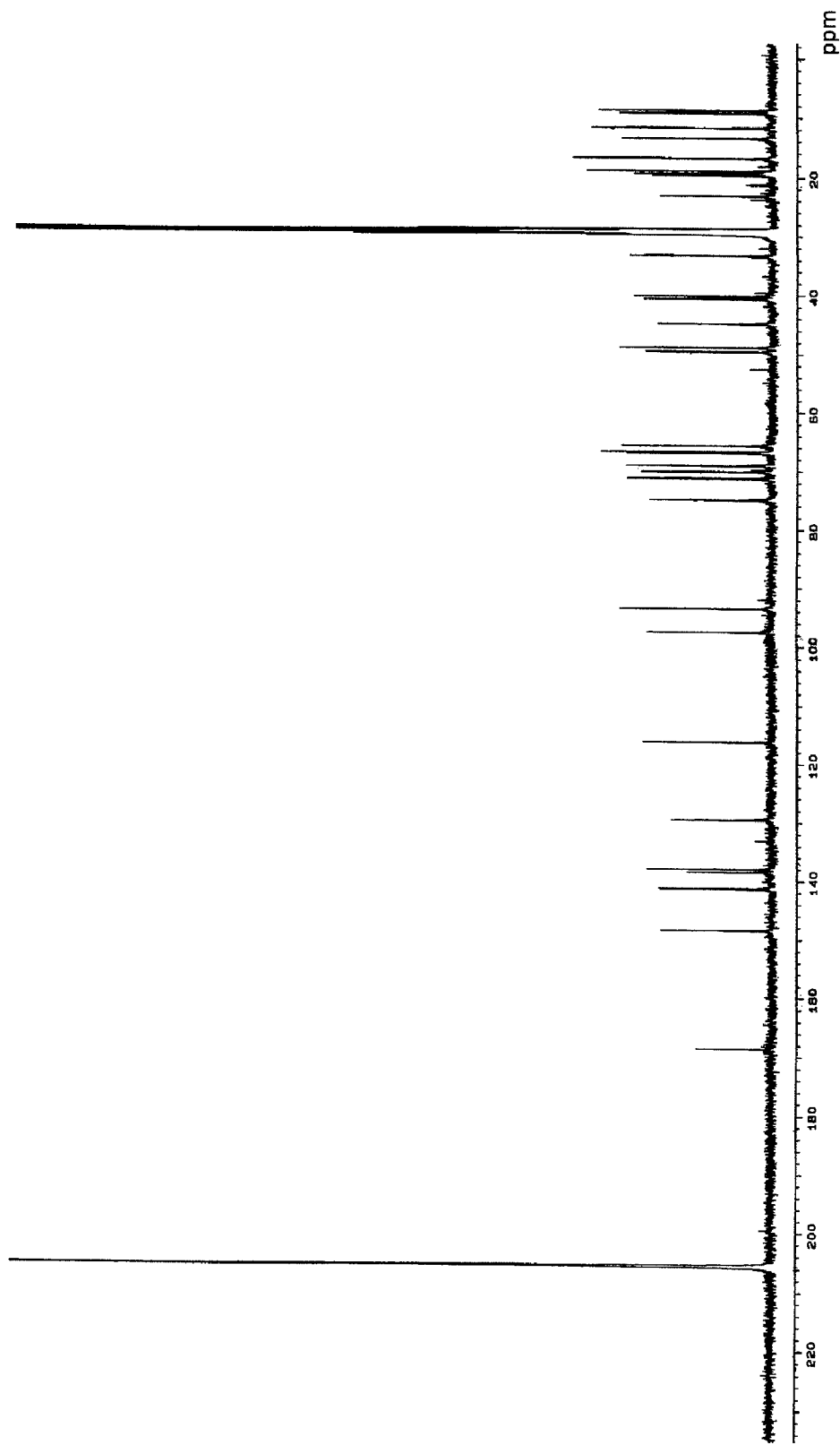
FIG. 3 is $^{13}$C-nuclear magnetic resonance spectrum of bispolide A1 as measured in acetone-$d_6$ solution at 125 MHz at room temperature.
Figure 4:
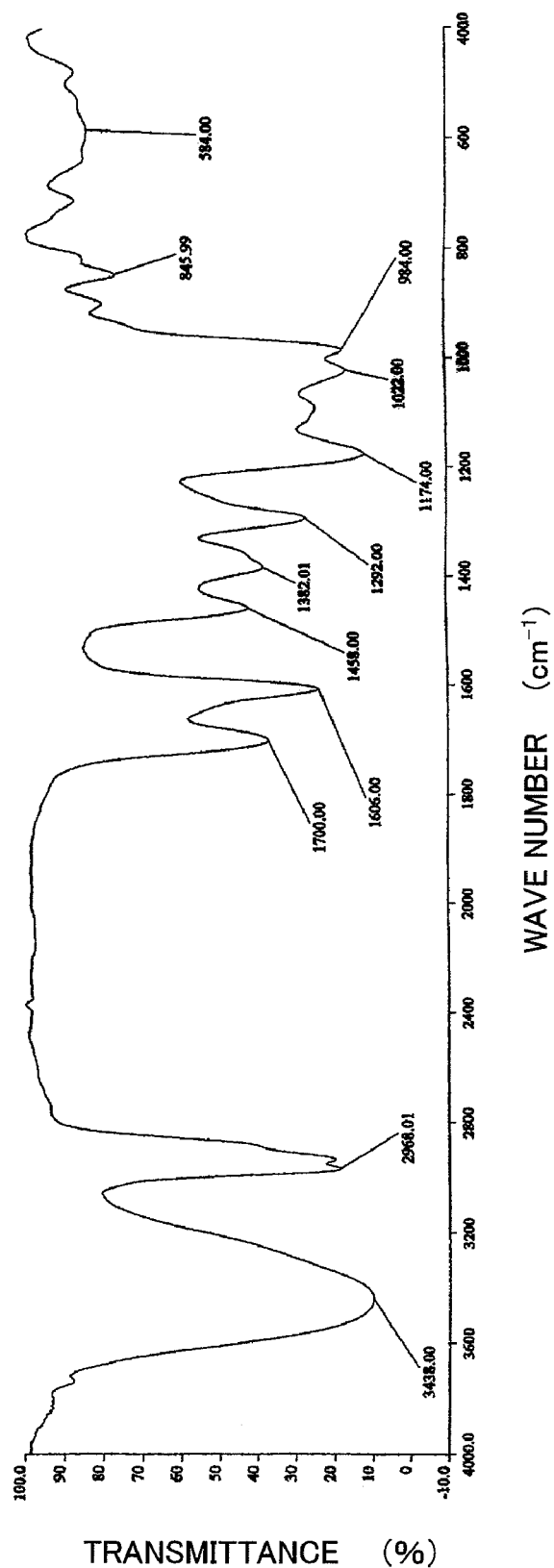
FIG. 4 is infrared absorption spectrum of bispolide A2 as measured by KBr-tableted method.
Figure 5:
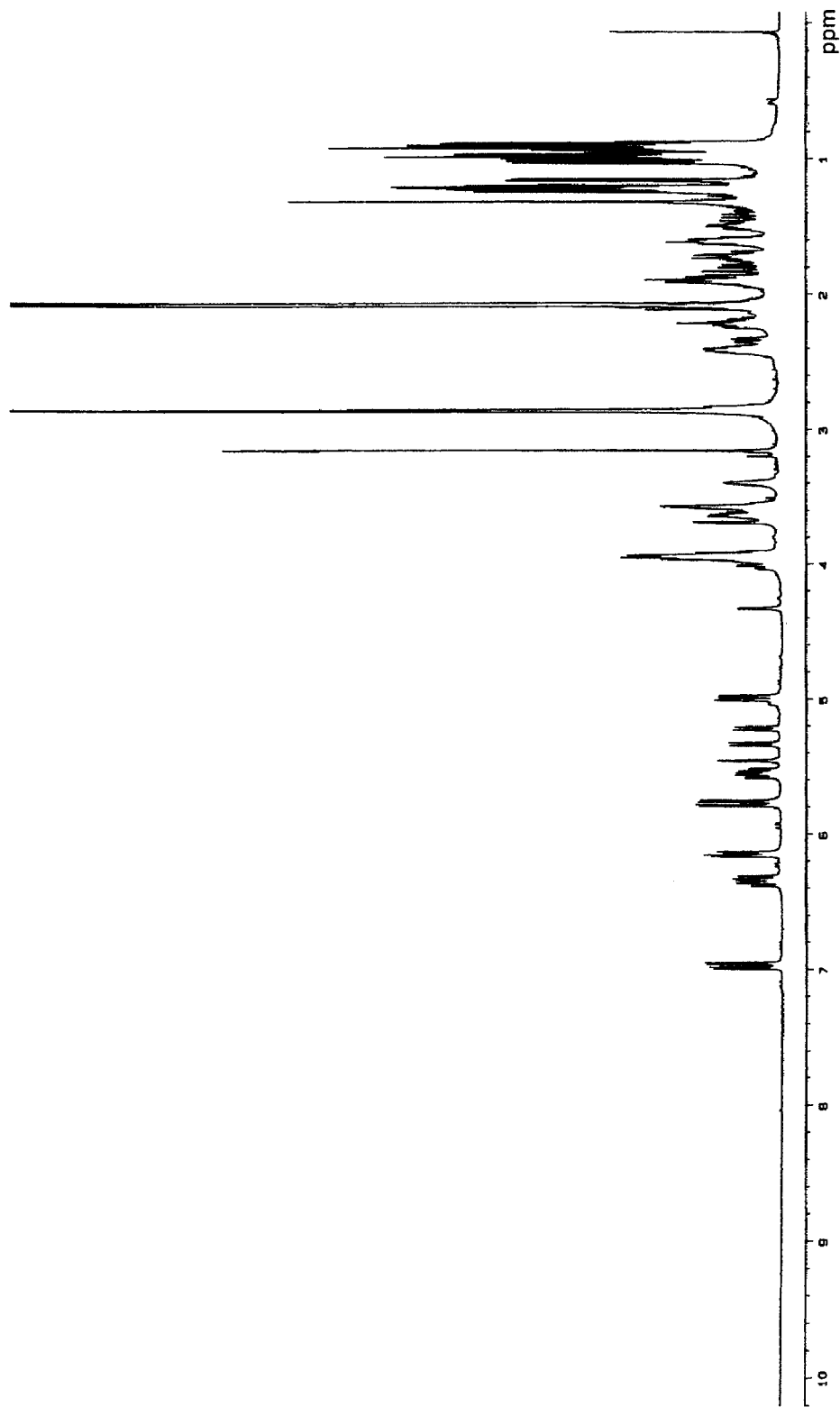
FIG. 5 is proton nuclear magnetic resonance spectrum of bispolide A2 as measured in acetone-$d_6$ solution at 500 MHz at room temperature.
Figure 6:
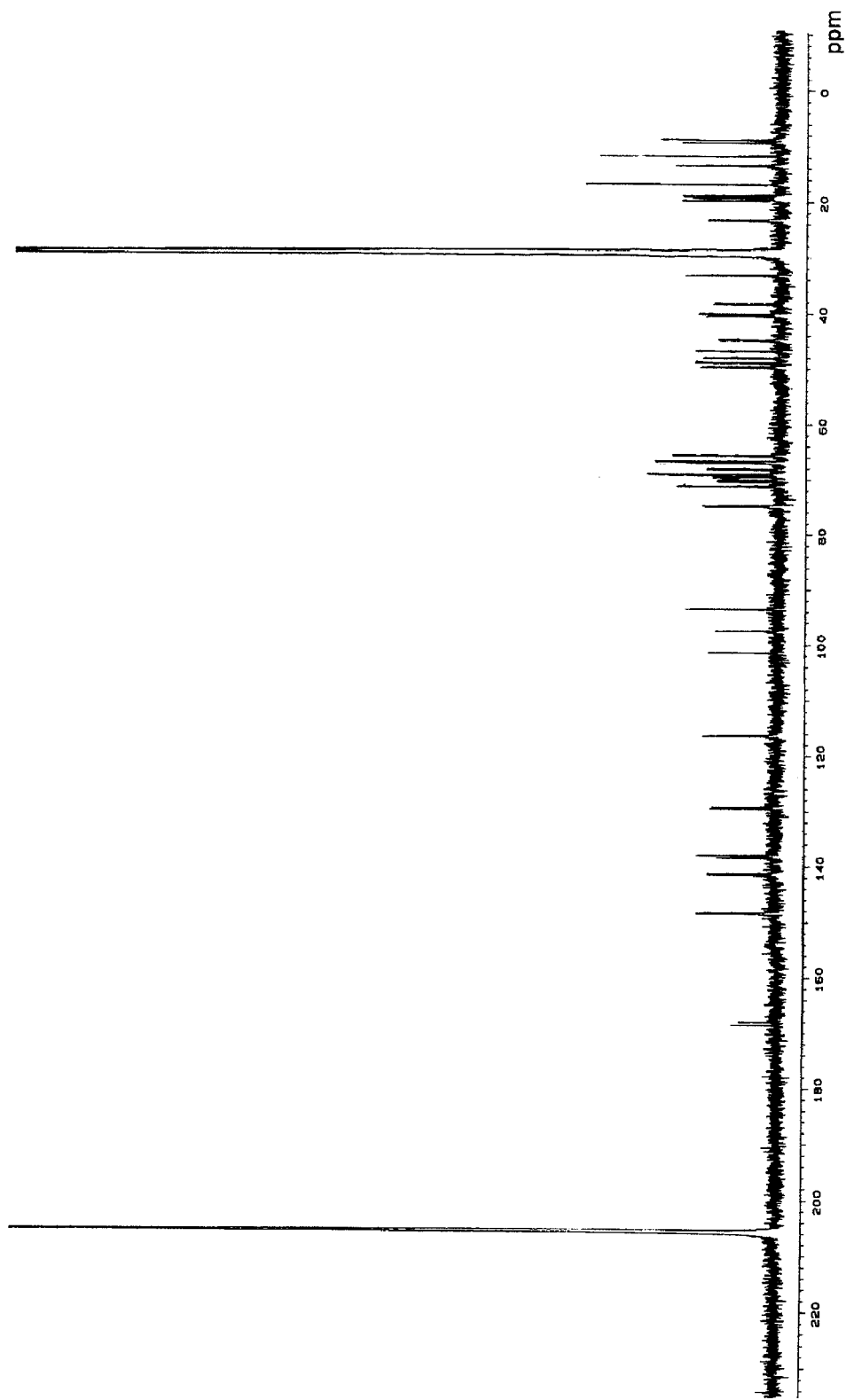
FIG. 6 is $^{13}$C-nuclear magnetic resonance spectrum of bispolide A2 as measured in acetone-$d_6$ solution at 125 MHz at room temperature.
Figure 7:
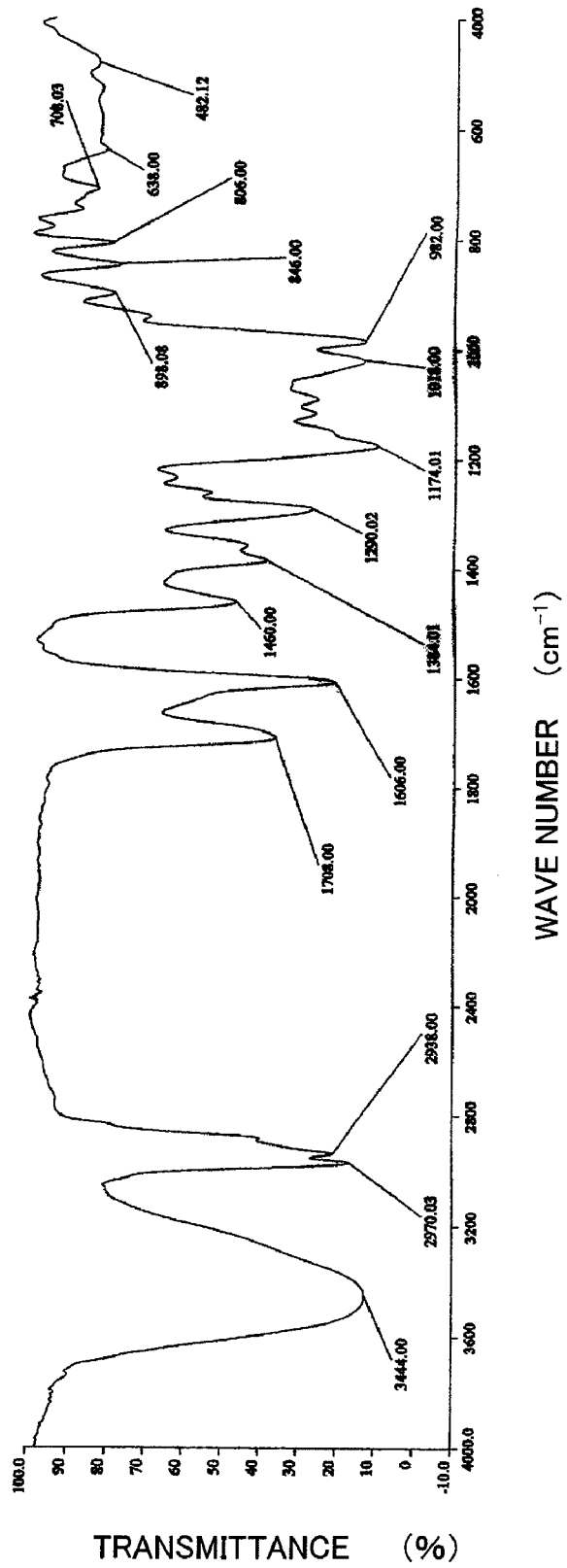
FIG. 7 is infrared absorption spectrum of bispolide A3 as measured by KBr-tableted method.
Figure 8:
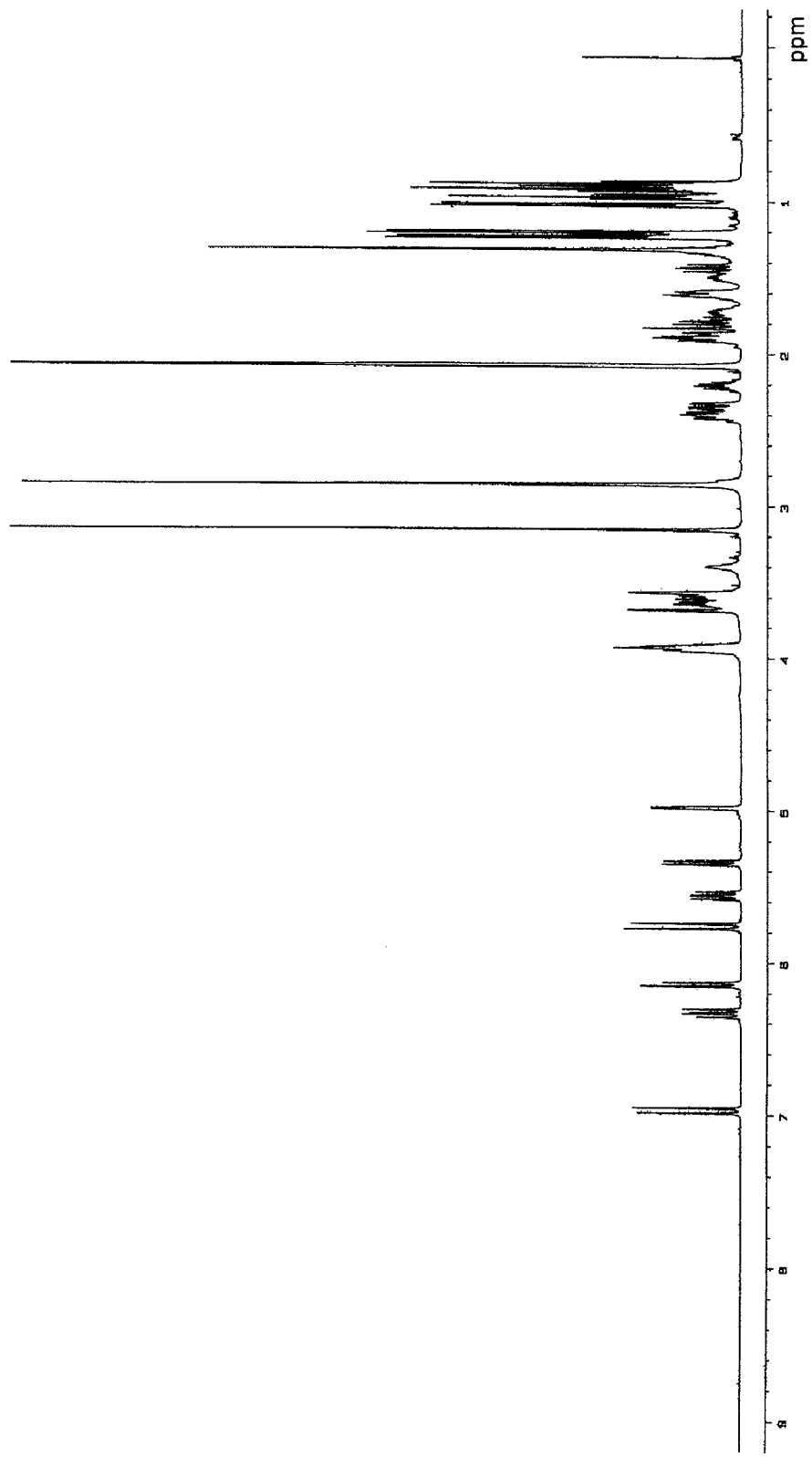
FIG. 8 is proton nuclear magnetic resonance spectrum of bispolide A3 as measured in acetone-$d_6$ solution at 500 MHz at room temperature.
Figure 9:
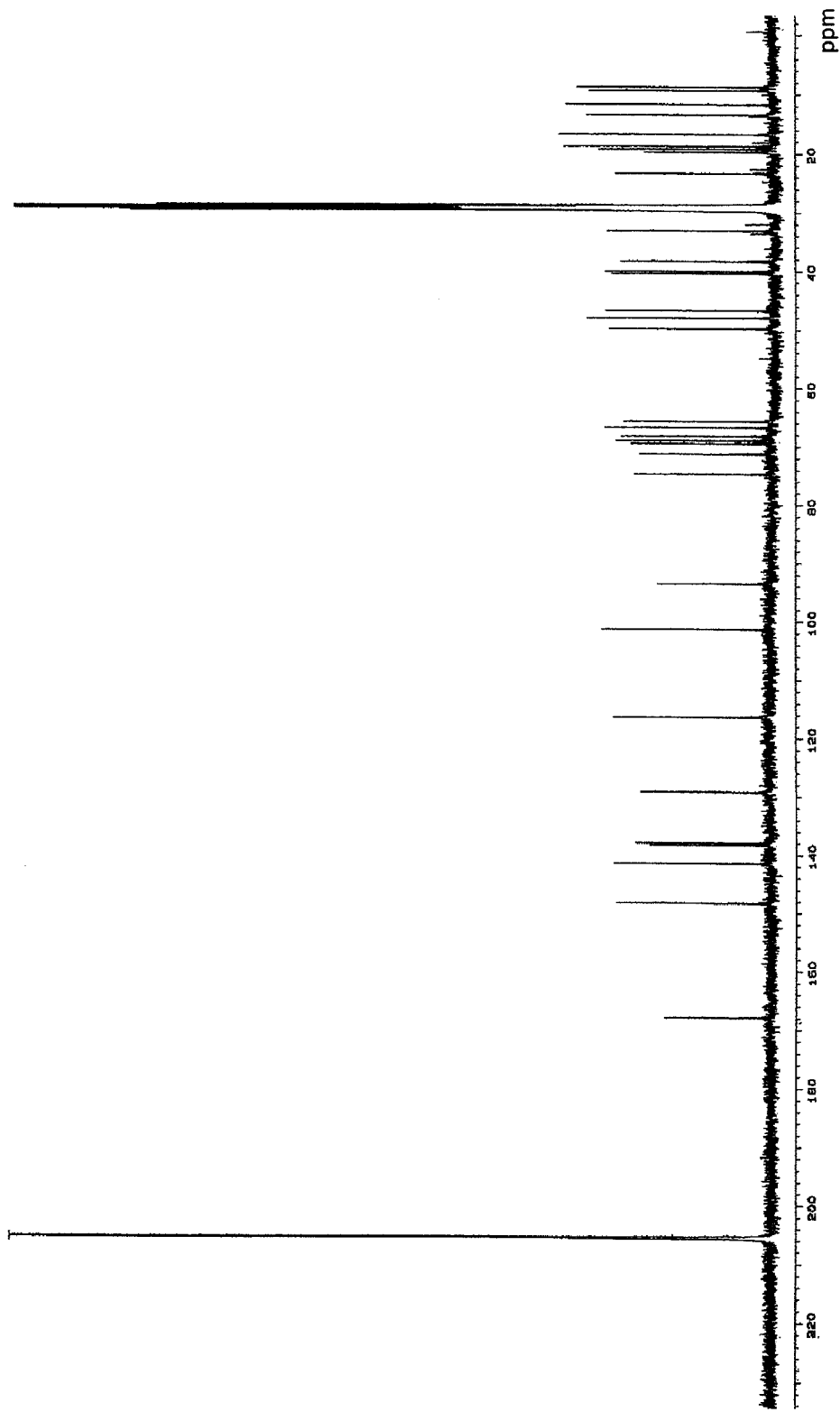
FIG. 9 is $^{13}$C-nuclear magnetic resonance spectrum of bispolide A3 as measured in acetone-$d_6$ solution at 125 MHz at room temperature.
Figure 10:
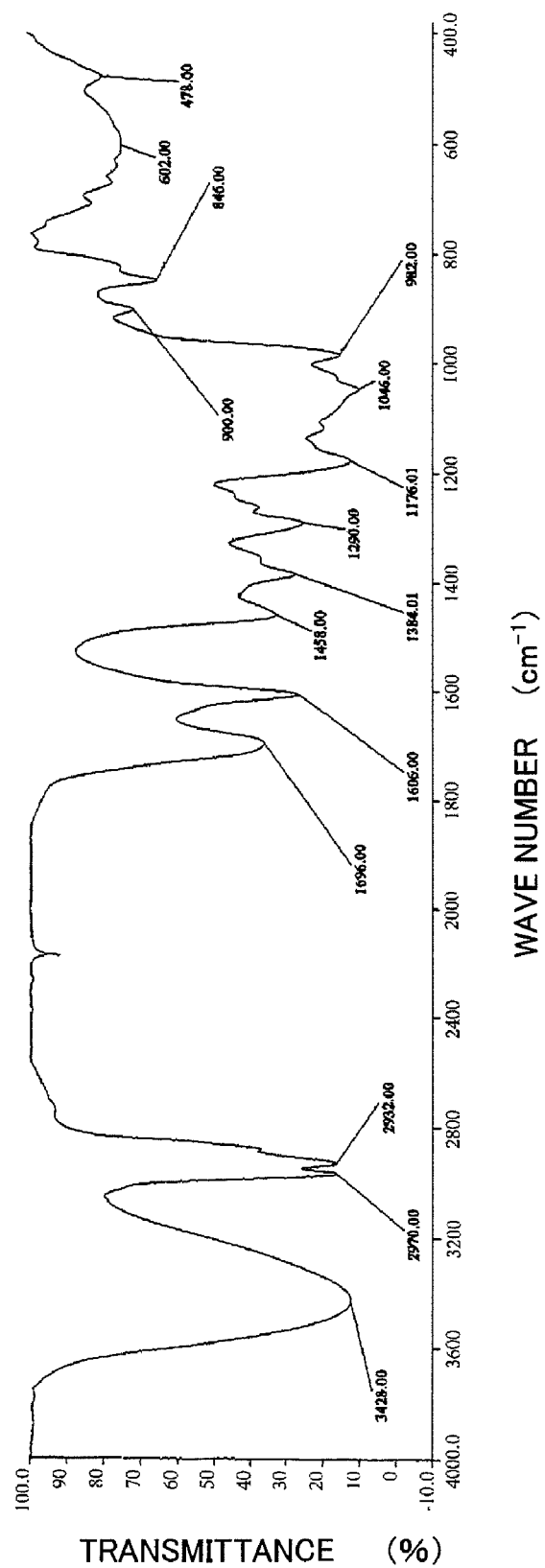
FIG. 10 is infrared absorption spectrum of bispolide B1 as measured by KBr-tableted method.
Figure 12:
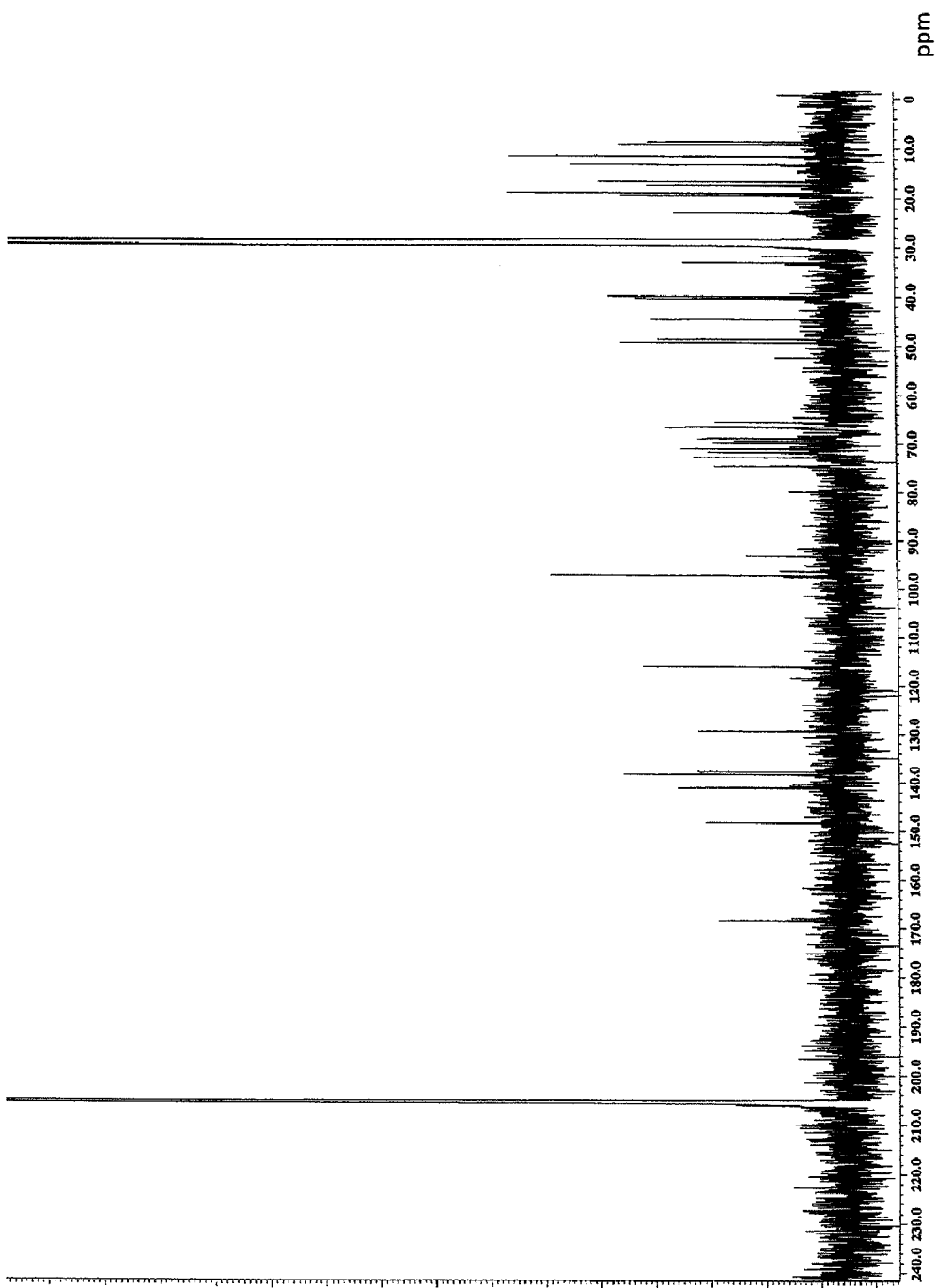
FIG. 12 is $^{13}$C-nuclear magnetic resonance spectrum of bispolide B1 as measured in acetone-$d_6$ solution at 100 MHz at room temperature.
Figure 13:
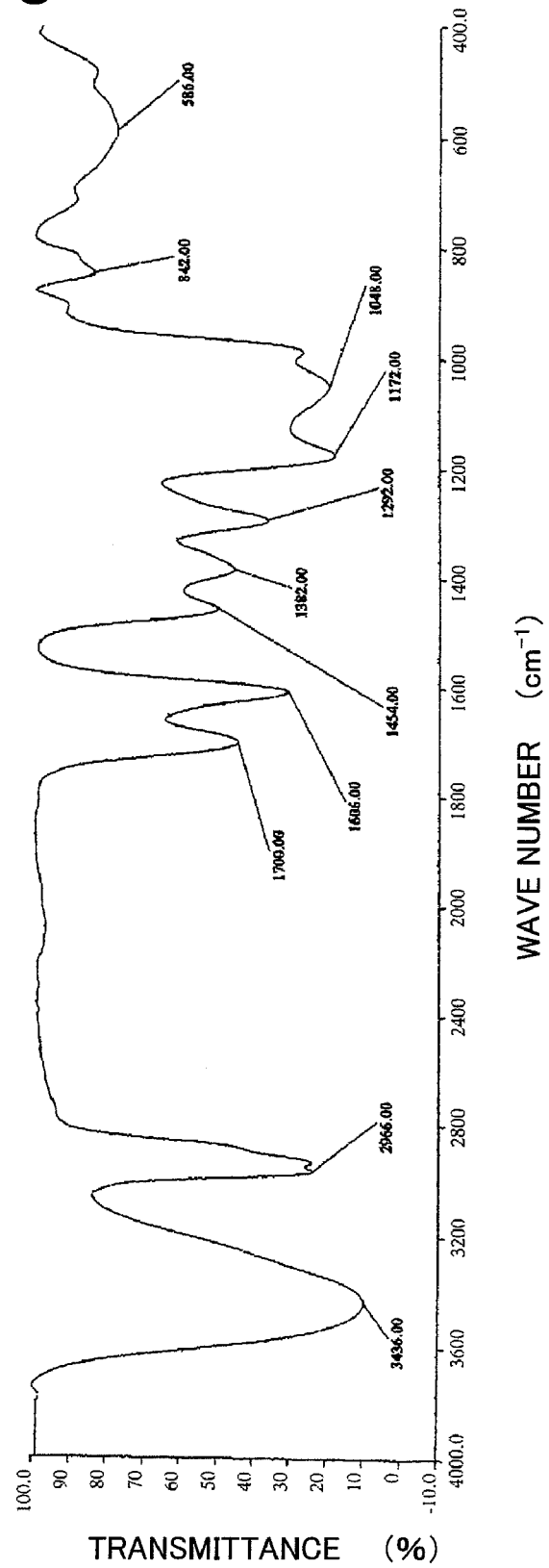
FIG. 13 is infrared absorption spectrum of bispolide B2a as measured by KBr-tableted method.
Figure 14:
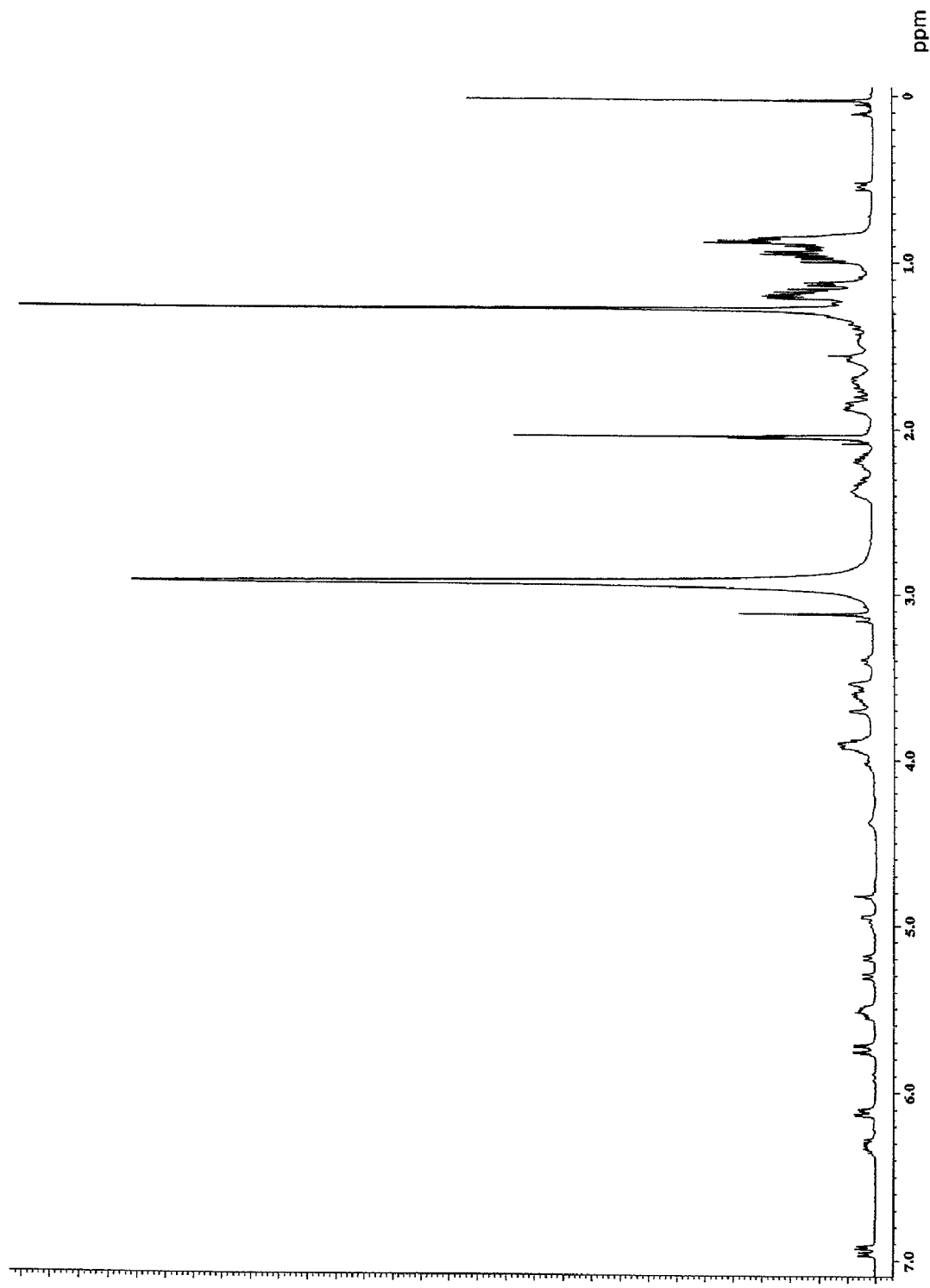
FIG. 14 is proton nuclear magnetic resonance spectrum of bispolide B2a as measured in acetone-$d_6$ solution at 400 MHz at room temperature.
Figure 15:
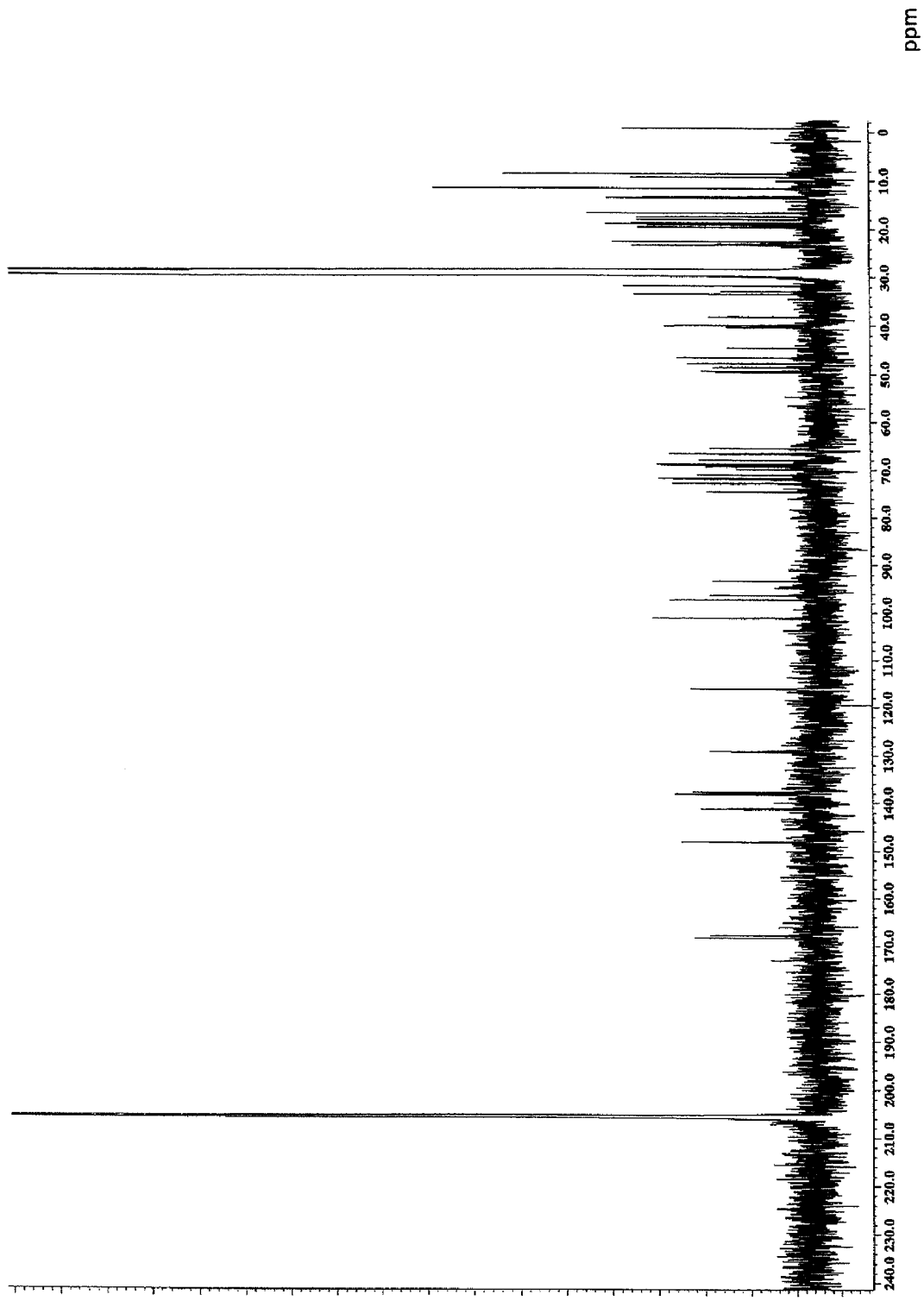
FIG. 15 is $^{13}$C-nuclear magnetic resonance spectrum of bispolide B2a as measured in acetone-$d_6$ solution at 100 MHz at room temperature.
Figure 16:
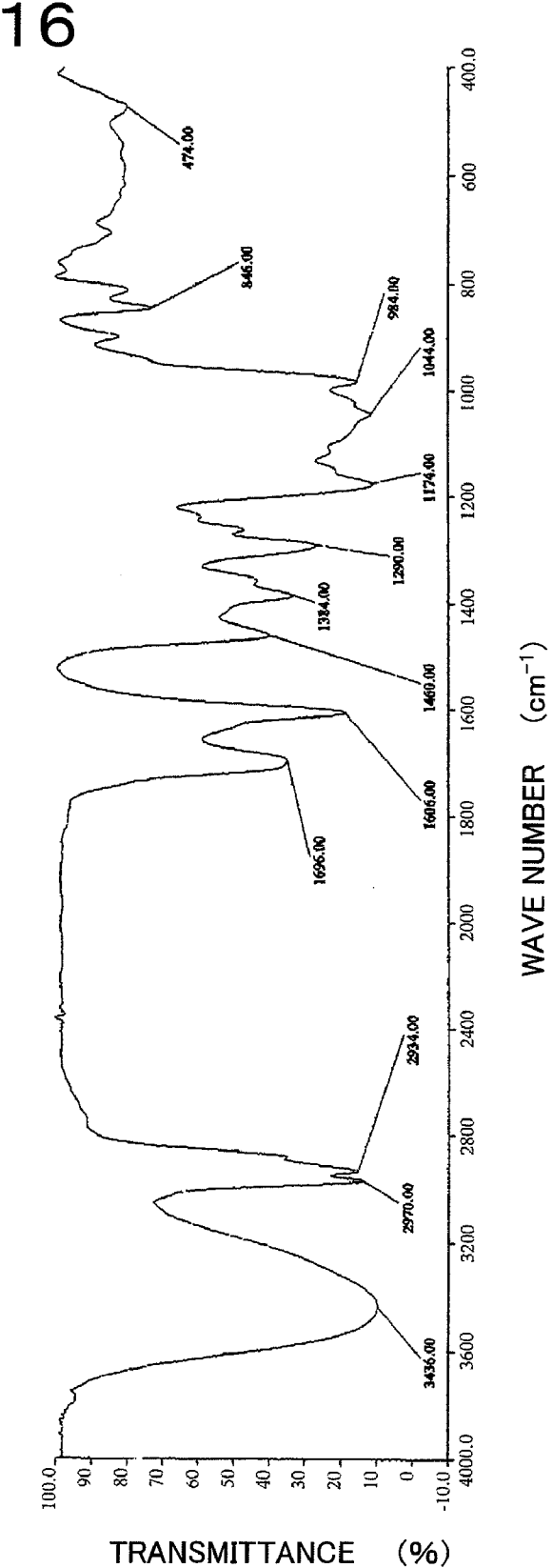
FIG. 16 is infrared absorption spectrum of bispolide B2b as measured by KBr-tableted method.
Figure 17:
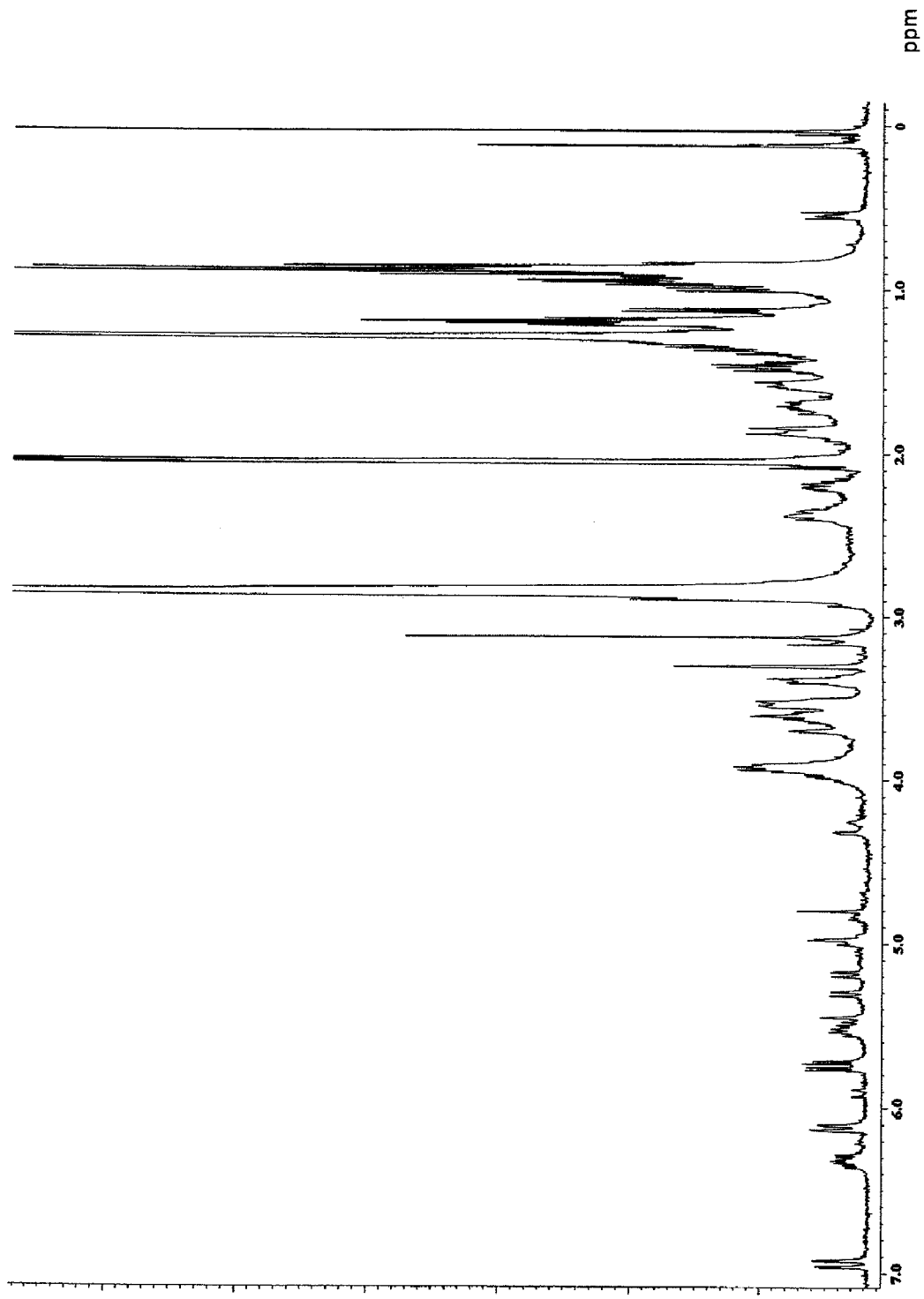
FIG. 17 is proton nuclear magnetic resonance spectrum of bispolide B2b as measured in acetone-$d_6$ solution at 400 MHz at room temperature.
Figure 18:
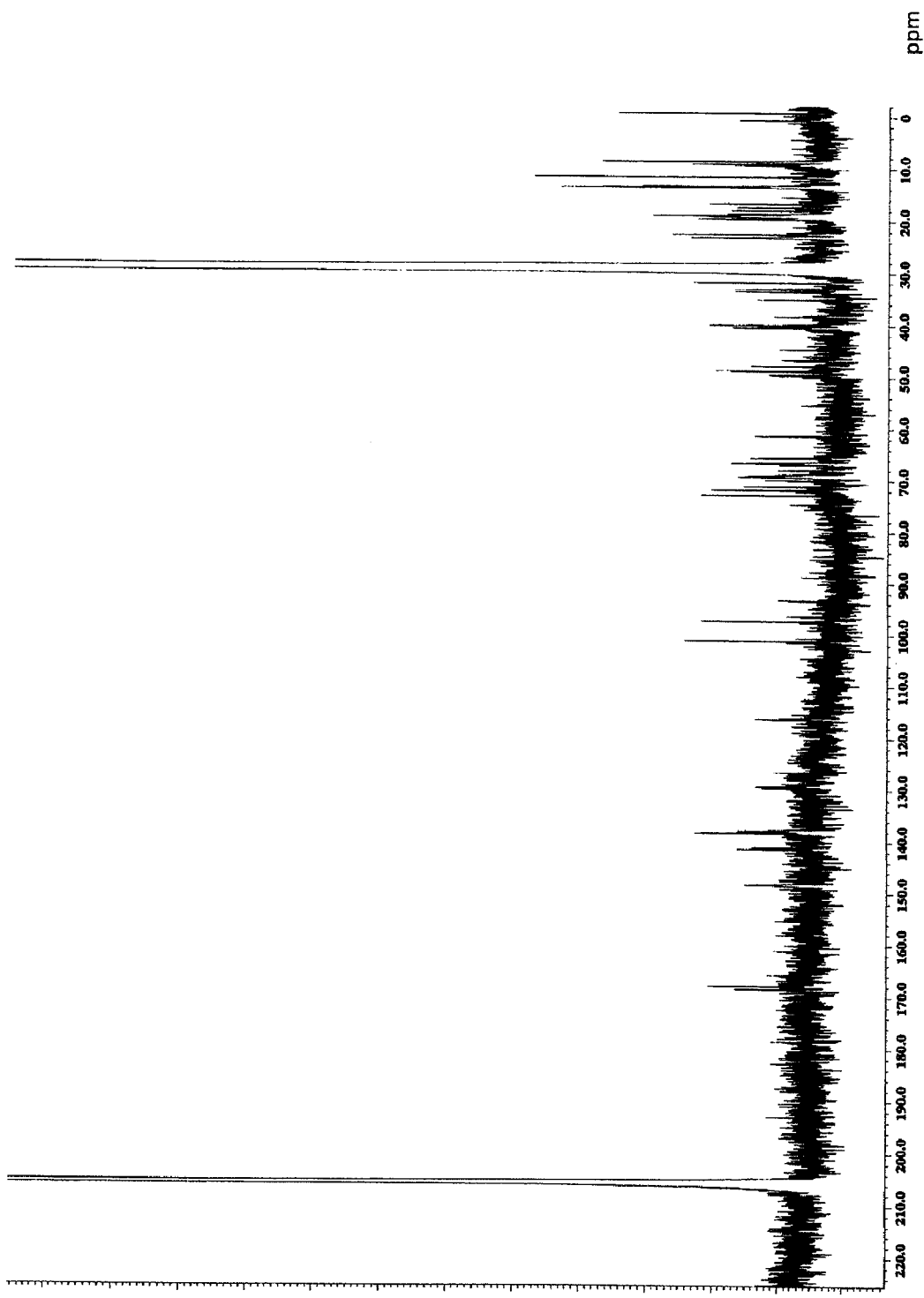
FIG. 18 is $^{13}$C-nuclear magnetic resonance spectrum of bispolide B2b as measured in acetone-$d_6$ solution at 100 MHz at room temperature.
Figure 19:
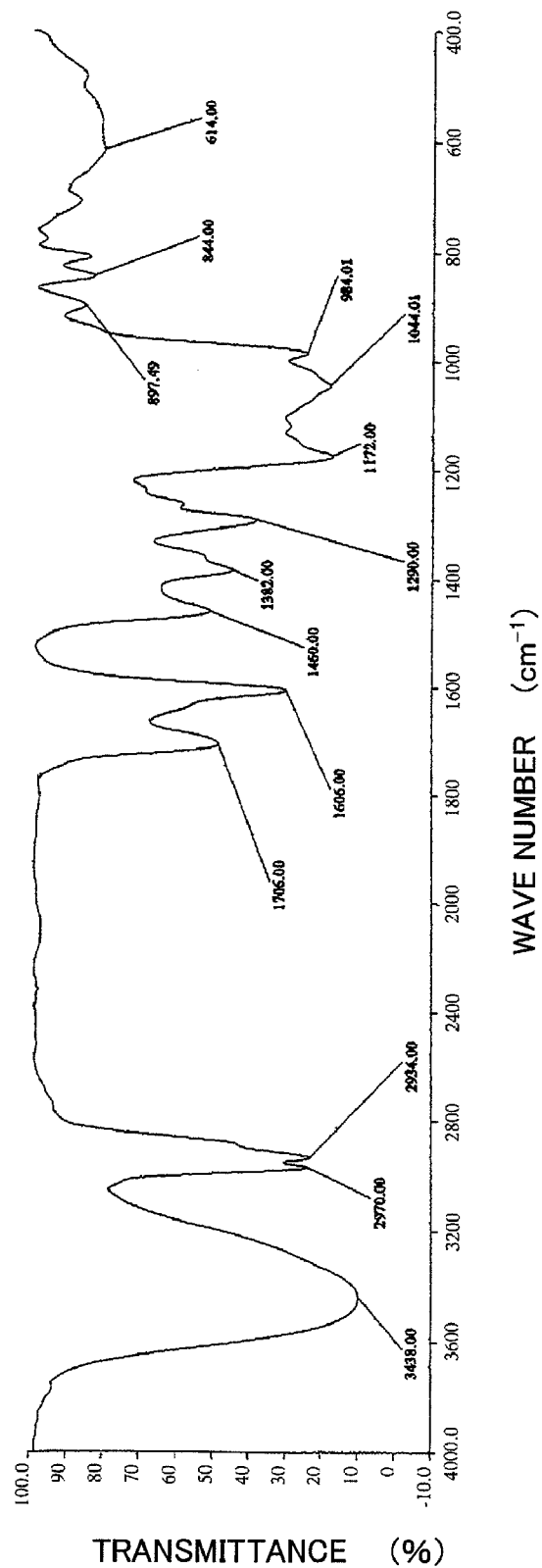
FIG. 19 is infrared absorption spectrum of bispolide B3 as measured by KBr-tableted method.
Figure 20:
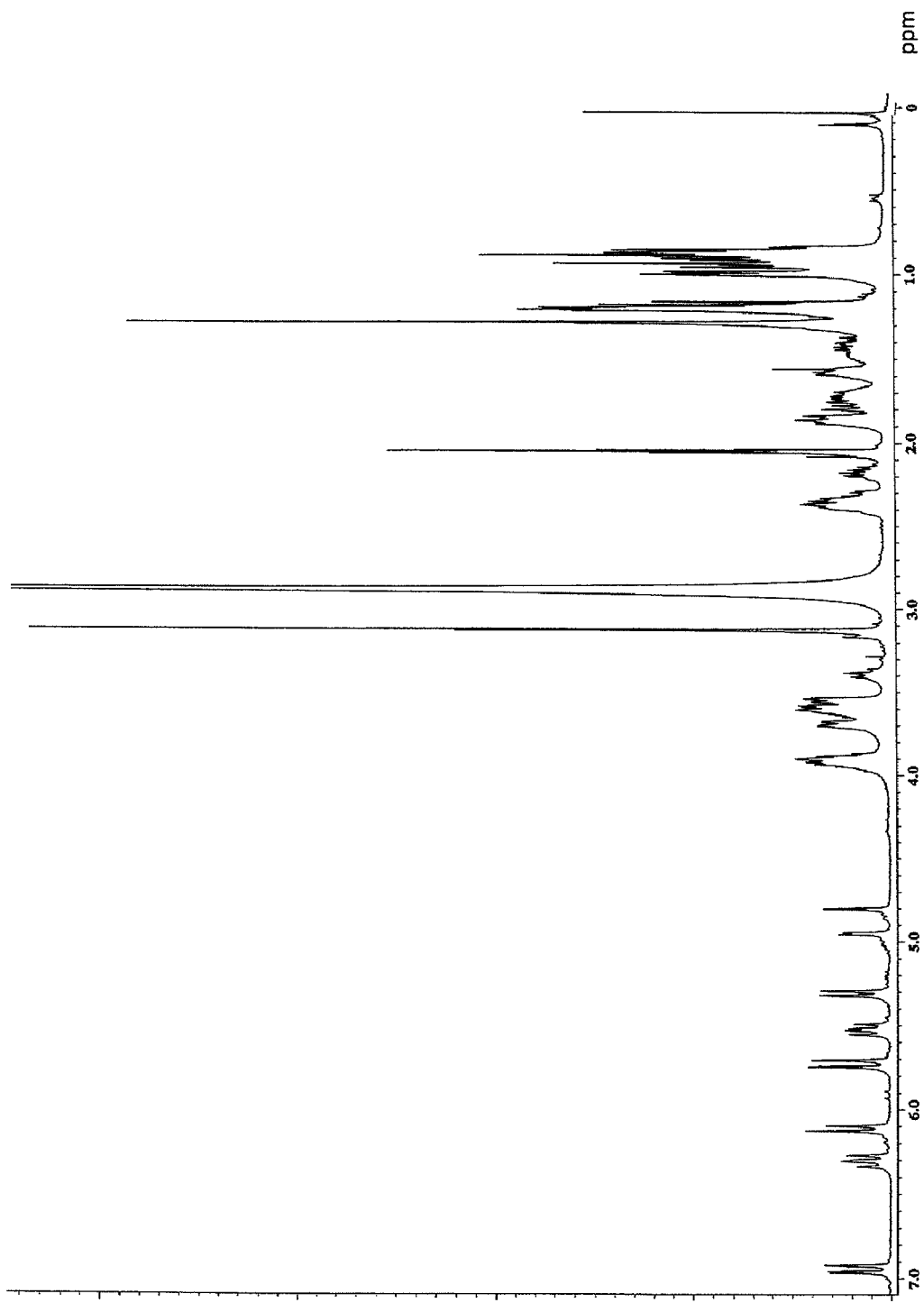
FIG. 20 is proton nuclear magnetic resonance spectrum of bispolide B3 as measured in acetone-$d_6$ solution at 400 MHz at room temperature.
Figure 21:
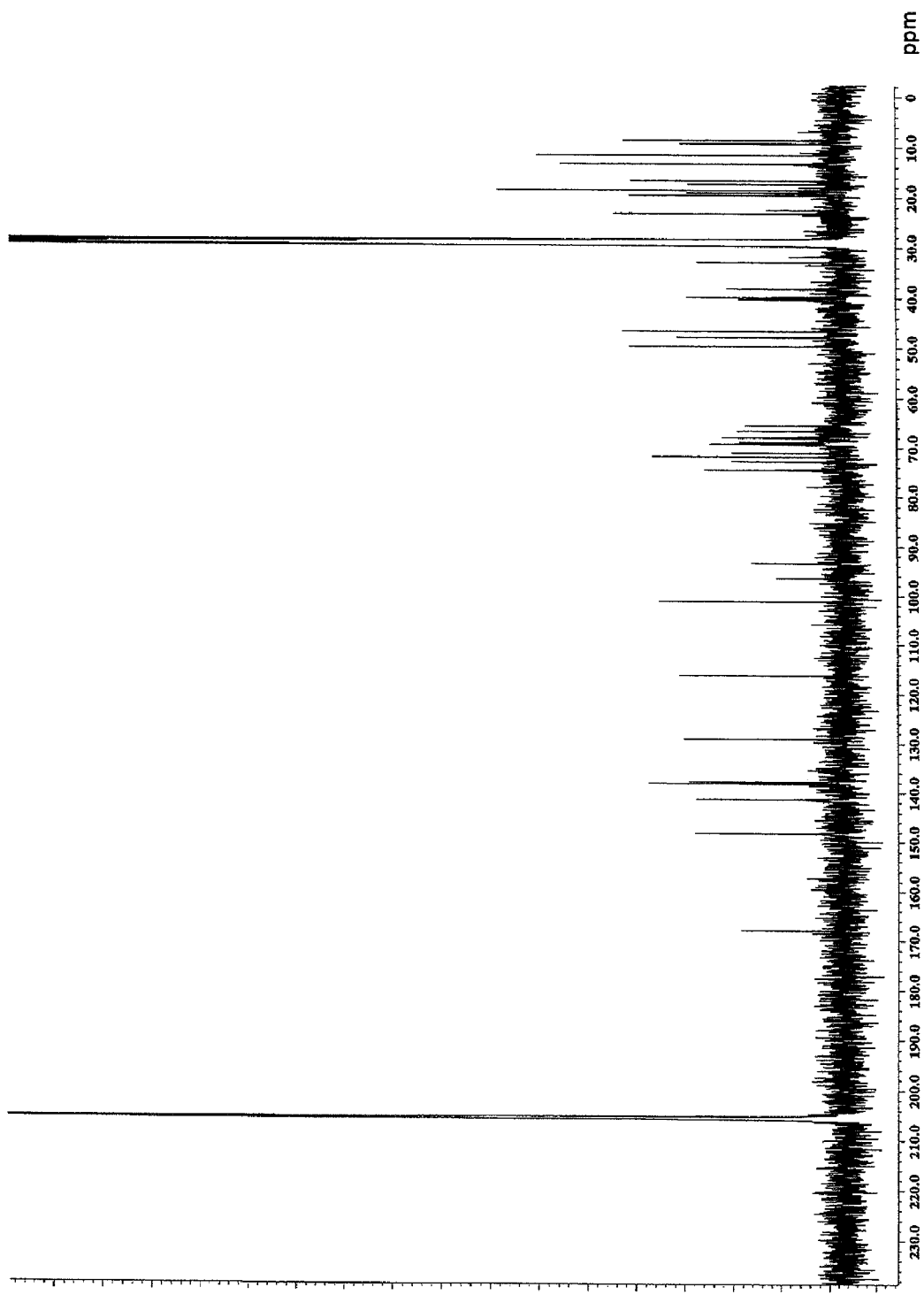
FIG. 21 is $^{13}$C-nuclear magnetic resonance spectrum of bispolide B3 as measured in acetone-$d_6$ solution at 100 MHz at room temperature.

This invention is now illustrated in more detail with reference to the following Example. The Example is only for the purpose of illustration and are not to be constructed as limiting the scope of this invention in any way.

EXAMPLE 1

Production of the Antibiotic, Bispolide A1, Bispolide A2 and Bispolide A3

A culture of the strain *Microbispora* sp. A34030 (deposited under the deposit number of FERM BP-10505), which had been cultured on the agar slant culture medium, was inoculated in a culture medium. This culture medium used here had been prepared by placing into Erlenmeyer flasks (of 500 ml-capacity each) 100 ml-portions of a liquid culture medium comprising 2% soluble starch (a product of Merck Co., U.S.A.), 1% glucose, 0.5% NZ-amine (a product of WAKO Junyaku, Japan), 0.5% powdered yeast extract (a product of Difco Co.), 0.05% calcium chloride, 0.005% powdered vitamin B (a product of Fancl Foods, Japan) (adjusted a pH of 7.0), and sterilizing the culture medium (100 ml) in each of the flasks (of 500 ml-capacity each) at 120° C. for 20 minutes in a usual manner, before the inoculation of said strain A34030 was done. The liquid culture medium so inoculated by said strain was then subjected to a shaking cultivation with a rotation speed of 225 rpm. at 28° C. for 9 days, thereby to afford a seed culture broth as intended.

In 40 Erlenmeyer flasks (of 500 ml-capacity each), there was prepared totally 4 liters of a culture medium (100 ml in each flask) comprising 2% corn starch, 3% soybean powder, 1% calcium carbonate and 0.1% palm oil molasses (adjusted to a pH of 7.4), which was then sterilized for 20 min. at 120° C., so as to afford the productive culture medium. To this productive culture medium present in the flasks, there were each inoculated 1 ml-portion of the above-mentioned seed culture broth.

The cultivation of the strain A34030 was conducted under the conditions that the cultivation was effected for 12 days at a temperature of 28° C. with shaking at a rotation speed of 225 rpm.

The resulting culture broth was then centrifuged to separate into the culture broth supernatant and the cultured microbial cells. Subsequently, methanol (100 ml) was added to the microbial cells so separated, and the resultant mixture was well stirred to extract the bispolide A from the cells into methanol. This extraction was done twice and the resultant methanolic extracts were combined together and concentrated to 50-ml volume under a reduced pressure. The resulting concentrated solution (50 ml) so obtained was extracted with ethyl acetate (150 ml), and the extract in ethyl acetate was concentrated to dryness under a reduced pressure after said extract had been dried with anhydrous sodium sulfate, followed by filtration.

The solid residue obtained as above comprised a crude mixture of bispolide A1, bispolide A2 and bispolide A3, and this solid residue was chromatographed by passing a solution of said solid residue (about 450 mg) in 2 ml of ethyl acetate through a silica gel column comprising 15 g of silica gel (Art 1.07734.1000, a product of Merck Co., U.S.A.) to make the bispolide A adsorbed by the silica gel, and then washing the silica gel column with chloroform (280 ml), and subsequently developing the column successively with the 24 ml-portions of the development solvents, namely chloroform-methanol (100:1 by volume); chloroform-methanol (50:1 by volume); chloroform-methanol (25:1 by volume); chloroform-methanol (25:2 by volume); chloroform-methanol (25:4 by volume); and chloroform-methanol (25:8 by volume) in this order. The resultant eluates were collected in 5 ml-fractions. The antibacterially active fractions containing bispolides A1, A2 and A3 could be harvested by eluting the silica gel column with the solvent of chloroform-methanol (25:4 by volume) and with the solvent of chloroform-methanol (25:8 by volume)??.

The antibacterially active fractions were combined together, and the solution so combined was concentrated under a reduced pressure, affording 92.4 mg of a light brown colored syrupy residue comprising a crude product of a bispolide A.

This syrupy residue was purified by subjecting to a preparative liquid chromatography with using a column (21.4 mm in diameter×100 mm height) commercially available under a trade name "Varian Microsorb", where the stationary phase of said column comprised 3 micron-diameter particles of Microsorb C18 Prep. (a commercially available product of Varian Palo Alto, Calif., U.S.A.). In this chromatographic procedure, there was used the mobile phase (0.2 ml) made of mixtures of $CH_3CN$ and $H_2O$ with concentration gradients of 70:30 to 80:20 ratios (by volume) at the eluation speed of 5 ml/minute Bispolide A1, bispolide A2 and bispolide A3 were eluted out respectively at the retention times of 25 minutes, 48 minutes and 81 minutes. The active eluate containing bispolide A1, the active eluate containing bispolide A2 and the active eluate containing bispolide A3 were separately collected and concentrated to dryness under a reduced pressure, respectively, to afford 12.2 mg of a white colored powdery pure product of bispolide A1, 7.5 mg of a white colored powdery pure product of bispolide A2 and 14.7 mg of a white colored powdery pure product of bispolide A3, which have been confirmed experimentally to exhibit the aforesaid physicolchemical properties and biological properties of them.

EXAMPLE 2

(a) Production of the New Antibiotic, a Bispolide B Along with Production of a Bispolide A, Followed by Recovery of Bispolides A and B A culture of the strain, *Microbispora* sp. A34030 (deposited under the deposit number of FERM BP-10505), which had been cultured on the agar slant culture medium, was inoculated to a culture medium. This culture medium used here had been prepared by placing into Erlenmeyer flasks (of 500 ml-capacity each) 100 ml-portions of a liquid culture medium comprising 2% soluble starch (a product of Merck Co. U.S.A.), 1% glucose, 0.5% NZ-amine (a product of WAKO Junyaku, Japan), 0.5% powdered yeast extract (a product of Difco Co.), 0.05% calcium chloride, 0.005% powdered vitamin B (a product of Fancl Foods) (adjusted a pH of 7.0), and sterilizing the culture medium (100 ml) in each of the flasks (of 500 ml-capacity each) at 120° C. for 20 minutes in a usual manner, before the inoculation of said strain A34030 was done. The liquid culture medium so inoculated by said strain was then subjected to a shaking cultivation with a rotation speed of 225 rpm. at 28° C. for 9 days, thereby to afford a seed culture broth as intended.

In 40 Erlenmeyer flasks (of 500 ml-capacity each), there was prepared totally 4 liters of a culture medium (100 ml-portion in each flask) comprising 1% glucose, 1% cotton seed meal, 1% powdered yeast extract and 0.2% calcium carbonate (adjusted to a pH of 7.0), which was then sterilized for 20 minutes at 120° C., so as to afford the productive culture medium. To this productive culture medium present in the Erlemeyer flasks, there were each inoculated 1 ml-portion of the above-mentioned seed culture broth. The cultivation of the strain A34030 was conducted under the conditions that the cultivation was effected for 12 days at a temperature of 28° C. with rotatory shaking at a speed of 225 rpm. The resulting culture broth was then centrifuged to separate it into the culture broth supernatant and the cultured microbial cells. Subsequently, methanol (100 ml) was added to the microbial cells so separated, and the resultant mixture was well stirred to extract the bispolide B and bispolide A from the cells into methanol. This extraction was done twice and the resultant methanolic extracts were combined together and concentrated to 50-ml volume under a reduced pressure. The resulting concentrated solution (50 ml) so obtained was extracted with ethyl acetate (150 ml), and the resulting extract in ethyl acetate was dried with anhydrous sodium sulfate and then filtered. Next, the dried extract filtrate was concentrated to dryness under a reduced pressure.

The solid residue obtained as above comprised a crude mixture containing bispolide A1, bispolide A2 and bispolide A3 as well as bispolide B1, bispolide B2a, bispolide B2b and bispolide B3. This solid residue (about 450 mg) was chromatographed by passing a solution of said solid residue dissolved in 20 ml of ethyl acetate, through a silica gel column comprising silica gel (Art 1.07734.1000, a product of Merck Co., U.S.A.) to make the bispolide A and bispolide B adsorbed by the silica gel, then washing the silica gel column with chloroform (200 ml), and subsequently developing this column successively with the different development solvents, namely chloroform-methanol (50:1 by volume, 200 ml); chloroform-methanol (25:1 by volume, 156 ml) and chloroform-methanol (25:4 by volume, 120 ml) in this order. The antibacterially active fractions containing bispolides A1, A2 and A3, as well as bispolides B1, B2a, B2b and B3 could be harvested by eluting the silica gel column with the solvent of chloroform-methanol (25:4 by volume).

The antibacterially active fractions were combined together, and the solution so combined was concentrated under a reduced pressure, affording 243 mg of a light brown colored syrupy residue comprising a crude mixture of bispolides A1 to A3 and bispolides B1 to B3.

(b) Isolation of the Antibiotics, Bispolide B1, Bispolide B2a, Bispolide B2b and Bispolide B3, and Isolation of Bispolides A1 to A3

The syrupy residue obtained in the above item (a) was purified by subjecting to a preparative liquid chromatography with using a chromatography column (21.2 mm in diameter× 150 mm in height) which is commercially available under a trade name "Agilent, ZORBAX XDB-C18 C18 Prep, PrepHT, 5 µm". In this chromatographic procedure, there was used the mobile phase made of mixtures of $CH_3CN$ and $H_2O$ with concentration gradients of 70:30 to 80:20 ratios (by volume) at the elution speed of 5 ml/minute.

Bispolide B1, bispolide B2a, bispolide B2b and bispolide B3 were eluted out separately, and also bispolides A1, bispolide A2 and bispolide A3 were eluted separately. The active eluate containing bispolide B1 at a retention time of 4.8 minutes, the active eluate containing bispolide B2a at a retention time of 9.7 minutes, the active eluate containing bispolide B2b at a retention time of 11.2 minutes and the active eluate containing bispolide B3 at a retention time of 23.6 minutes were separately collected, and each active eluate was then concentrated to dryness under a reduced pressure, respectively. In this way, there were afford 15.6 mg of a white-colored or colorless powdery pure product of bispolide B1 (mp. 119.9-121.2° C.), 19.8 mg of a white-colored or colorless powdery pure product of bispolide B2a (mp. 151.5-152.5° C.), 10.8 mg of a white-colored or colorless powdery pure product of bispolide B2b (mp. 156.2-160.0° C.) and 20.6 mg of a white-colored or colorless powdery pure product of bispolide B3 (mp. 131.5-134.0° C.), which each have been confirmed experimentally to exhibit the aforesaid physicolchemical properties and biological properties of them.

In the above-mentioned chromatographic procedure, bispolide A1, bispolide A2 and bispolide A3 were also eluted out at the retention times of 6.9 minutes, 15.5 minutes and 32.7 minutes, respectively. The active eluates containing bispolides A1, A2 and A3, respectively, were separately collected and concentrated to dryness under a reduced pressure to yield 28.8 mg of bispolide A1, 45.8 mg of bispolide A2 and 50.0 mg of bispolide A3, respectively.

EXAMPLE 3

This Example illustrates the production of an injectable preparation of the emulsion-type containing a bispolide compound of this invention as active ingredient.

(a) Production of an Intraperitoneally Injectable Liquid Preparation of the Emulsion-type A crystalline powder (800 mg) of bispolide A1 was dissolved in a volume (10 ml) of tertiary butanol, and the resulting solution of bispolide A1 was placed in 1 ml-portions in 10 sterile vials. The solution of bispolide A1 in these vials was concentrated to dryness under a reduced pressure and under the sterile conditions, followed by sealing the opening portions of these vials. Thereby, there were provided ten of the sealed and sterile vials each containing therein 80 mg of a finely divided powder of bispolide A1.

On the other hand, there were prepared ten of the sealed and sterile vials each containing therein 6 ml of 13% aqueous ethanol (namely, a mixture of 13 parts (by volume) of water with 87 parts (by volume) of anhydrous ethanol). Further, there were prepared ten of the sealed and sterile vials each containing therein 10 mg of "Polysorbate 80" which is known as a water-soluble emulsifier or solubilizing agent in the form of a non-ionic surfactant. This substance of "Polysorbate 80" is a commercially available product which is a liquid, polyoxyethylene ether compound such that is produced by etherifying with a polyoxyethylene (20) the esters as obtained by esterification of parts of the hydroxyl groups of anhydrous sorbitol with oleic acid. The bispolide A1 fine powder (80 mg) was taken out of one of the ten vials containing the fine powder of bispolide A1 as prepared in the above. Also, the 16% aqueous ethanol (6 ml) was taken out of one of the ten vials containing the 16% aqueous ethanol as prepared in the above. Further, "Polysorbate 80" (10 ml) was taken from one of the ten vials containing the "Polysorbate 80" as prepared in the above. Then, the bispolide A1 fine powder so taken out, the 16% aqueous ethanol so taken out, and the "Polysorbate 80" so taken out as above were uniformly mixed with each other under agitation and under the sterile conditions. In this way, there could be produced a colorless and liquid emulsion containing bispolide A1 therein. The liquid emulsion so produced is suitable for use as an intraperitoneally injectable preparation in the form of a dosage unit.

(b) Production of an Intravenously Injectable Preparation

About 6 ml of the colorless and liquid emulsion containing bispolide A1, which was produced in the above item (a), was mixed with 500 ml of physiological salt solution under agitation and under the sterile conditions. Thereby, there could be produced an aqueous suspension containing bispolide A1 therein. This aqueous suspension so produced is suitable as an injectable preparation which may be administered intravenously as drops.

Further, by the same procedures as described above, bispolides A2, A3, B1, B2a, B2b and B3 could respectively be formulated into an injectable preparation.

Industrial Applicability

As described hereinbefore, the bispolide A compound, namely bispolides A1, A2 and A3 having the general formula (I) as well as the bispolide B compound, namely bispolide B1, bispolide B2a, bispolide B2b and bispolide B3 having the general formula (II) are each an antibiotic substance which can collectively be represented by the general formula (III) above. The bispolide A compound and the bispolide B compound as obtained according to this invention each have excellent antibacterial activities against various bacteria, especially against Gram-positive bacteria, including antibiotic-resistant strains of the bacteria. Therefore, a bispolide A compound and a bispolide B compound according to this invention are each effective and useful for treating Gram-positive bacteria infections of human and animals.

The invention claimed is:

1. An antibiotic which is at least one of bispolide A1, bispolide A2, bispolide A3, bispolide B1, bispolide B2a, bispolide B2b and bispolide B3 that are each a compound represented by the following formula (III):

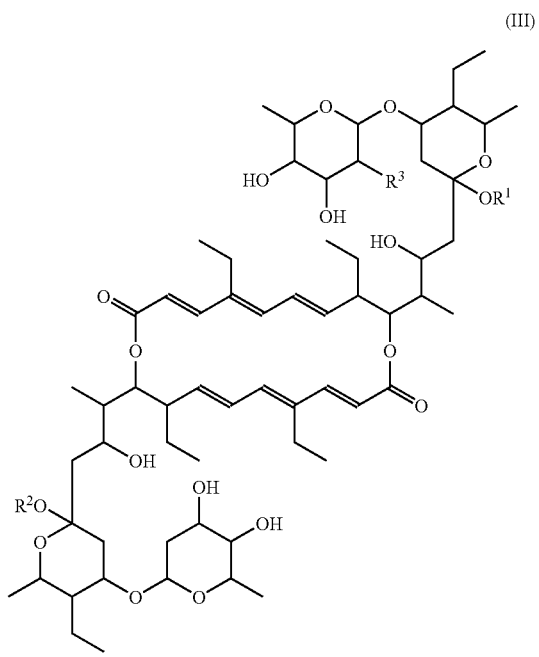

wherein $R^1$ and $R^2$ each denote a hydrogen atom or methyl group and $R^3$ denotes a hydrogen atom or a hydroxyl group, but wherein $R^1$ and $R^2$ are each a hydrogen atom and $R^3$ is a hydrogen atom for bispolide A1; $R^1$ is a hydrogen atom and $R^2$ is methyl group and $R^3$ is a hydrogen atom for bispolide A2; and $R^1$ and $R^2$ are each a methyl group and $R^3$ is a hydrogen atom for bispolide A3, and wherein $R^1$ and $R^2$ are each a hydrogen atom and $R^3$ is hydroxyl group for bispolide B1; $R^1$ is a hydrogen atom, $R^2$ is methyl group and $R^3$ is hydroxyl group for bispolide B2a; $R^1$ is methyl group, $R^2$ is a hydrogen atom and $R^3$ is hydroxyl group for bispolide B2b; and $R^1$ and $R^2$ are each a methyl group and $R^3$ is hydroxyl group for bispolide B3.

2. The antibiotic as claimed in claim 1, which is included in the antibiotic of the general formula (III) as defined in claim 1, and which is bispolide A1, bispolide A2 or bispolide A3 that is a compound represented by the following general formula (I):

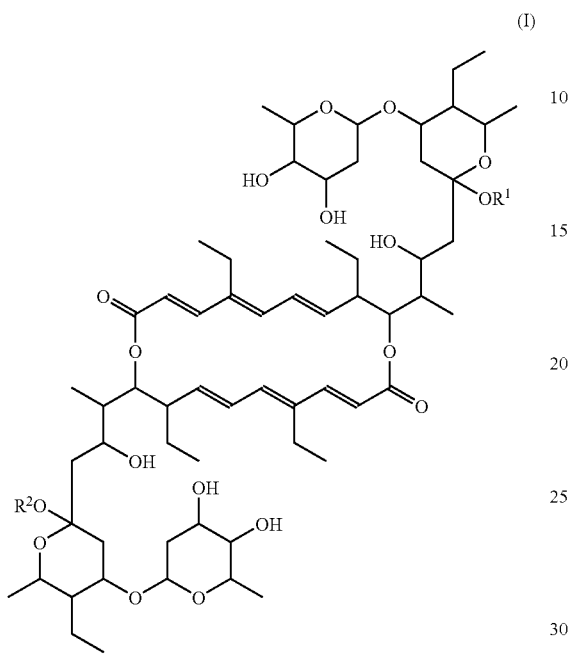

(I)

wherein $R^1$ and $R^2$ each denote a hydrogen atom or methyl group (—CH$_3$), and wherein $R^1$ and $R^2$ are each a hydrogen atom for bispolide A1; $R^1$ is a hydrogen atom and $R^2$ is a methyl group for bispolide A2; and $R^1$ and $R^2$ are each a methyl group for bispolide A3.

3. The antibiotic of claim 1, which is bispolide A1 of the following formula (Ia):

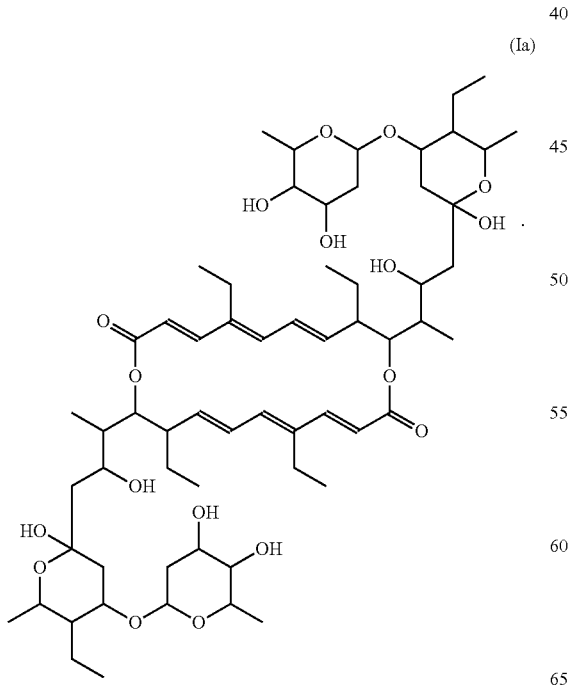

(Ia)

4. The antibiotic of claim 1, which is bispolide A2 of the following formula (Ib):

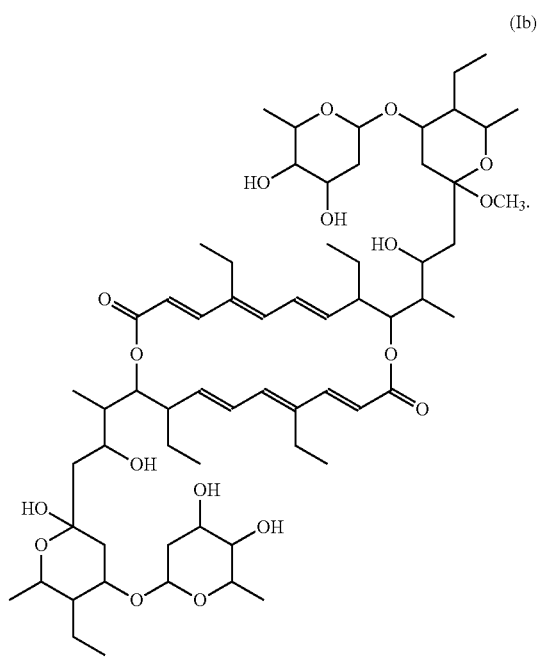

(Ib)

5. The antibiotic of claim 1, which is bispolide A3 of the following formula (Ic):

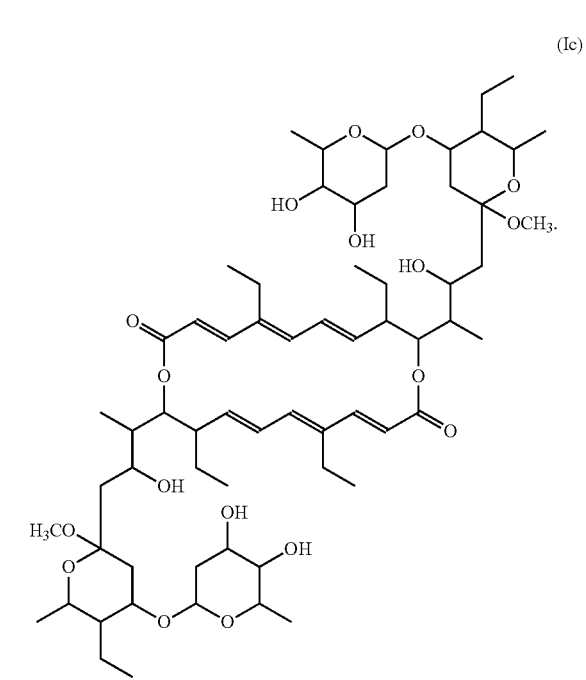

(Ic)

6. The antibiotic as claimed in claim 1, which is included in the antibiotic of the general formula (III) as defined in claim 1, and which is bispolide B1, bispolide B2a, bispolide B2b or bispolide B3 that is a compound represented by the following general formula (II):

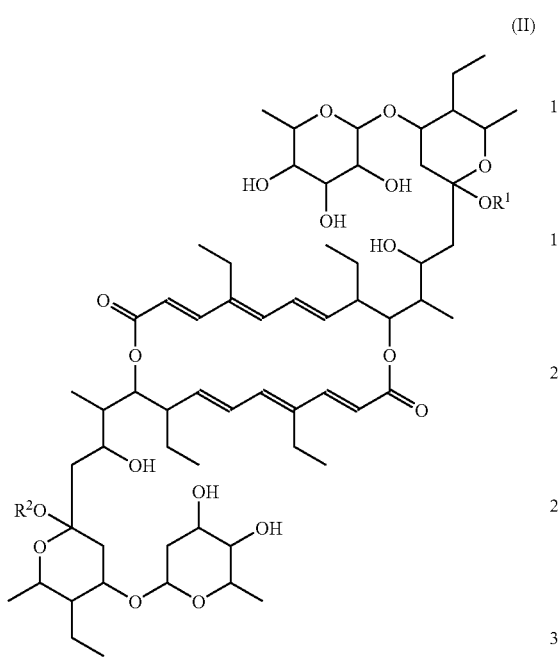

(II)

wherein $R^1$ and $R^2$ each denote a hydrogen atom or methyl group (—CH$_3$), and wherein $R^1$ and $R^2$ are each a hydrogen atom for bispolide B1; $R^1$ is a hydrogen atom and $R^2$ is a methyl group for bispolide B2a; $R^1$ is methyl group and $R^2$ is a hydrogen atom for bispolide B2b; and $R^1$ and $R^2$ are each a methyl group for bispolide B3.

7. The antibiotic of claim 1, which is bispolide B1 of the following formula (IIa):

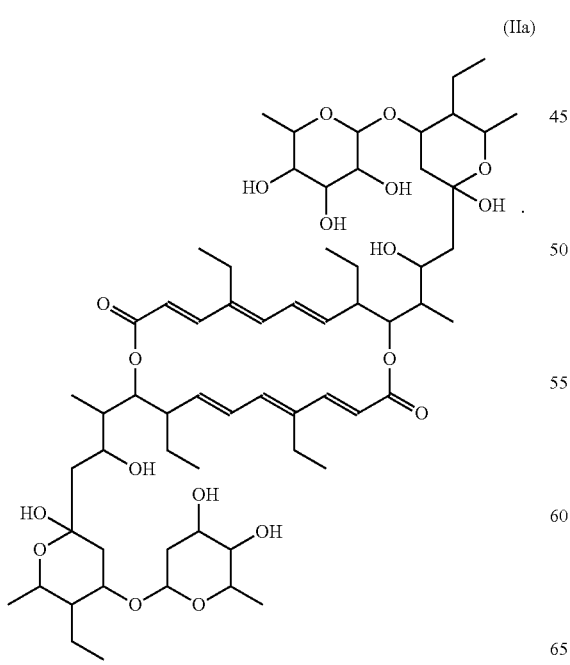

(IIa)

8. The antibiotic of claim 1, which is bispolide B2a of the following formula (IIb):

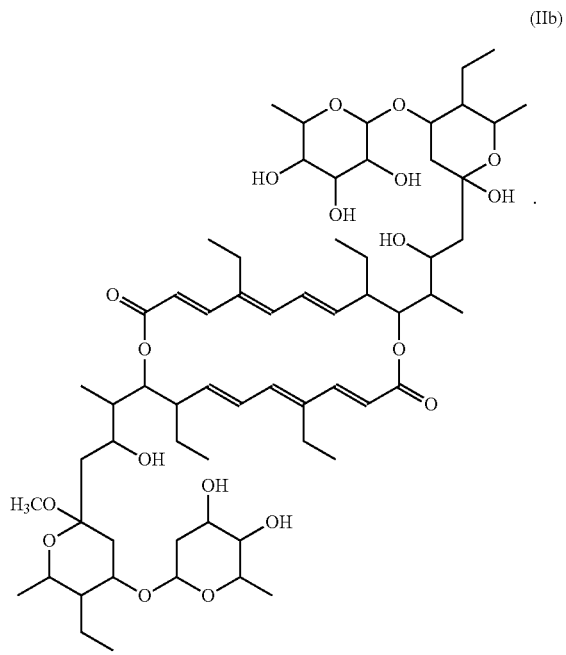

(IIb)

9. The antibiotic of claim 1, which is bispolide B2b of the following formula (IIc):

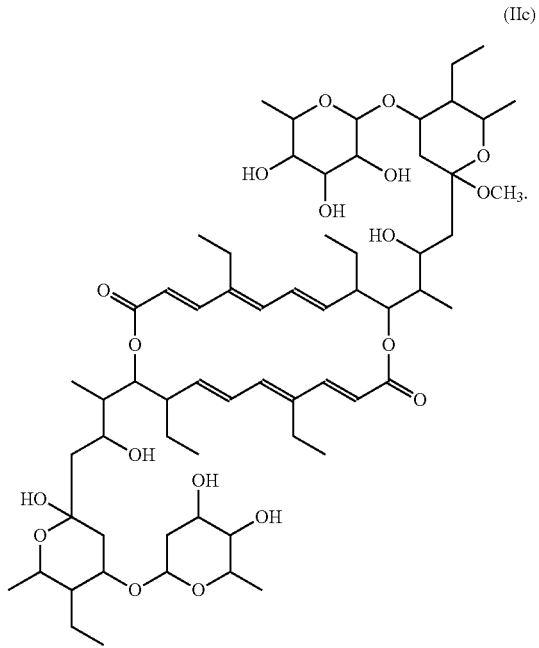

(IIc)

10. The antibiotic of claim 1, which is bispolide B3 of the following formula (IId):

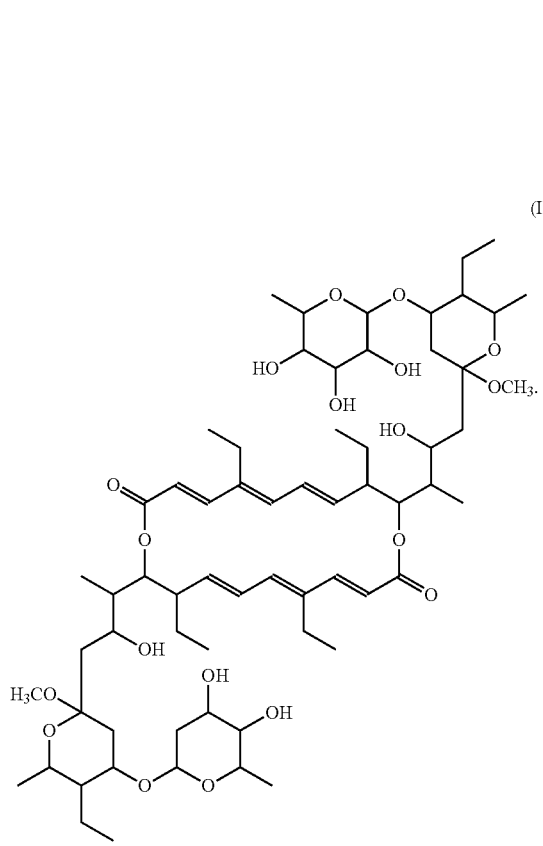

11. A process for the production of the antibiotic, bispolide A1, bispolide A2, bispolide A3, bispolide B1, bispolide B2a, bispolide B2b and/or bispolide B3 having the general formula (III) as defined in claim 1, which process comprises cultivating *Microbispora* sp. A34030 strain (deposited under the deposit number of FERM BP-10505) at a temperature of 25° C. to 30° C. for 3 days to 12 days in a culture medium which comprises the known carbon source, a nitrogen source and an inorganic salt to produce and accumulate at least one of bispolides A1, A2 and A3 as well as bispolides B1, B2a, B2b and B3 in the resulting culture, and recovering at least one of bispolide A1, bispolide A2, bispolide A3, bispolide B1, bispolide B2a, bispolide B2b and bispolide B3 from the resulting culture.

12. A process for the production of a bispolide A1 and/or a bispolide B, which process comprises cultivating *Microbispora* sp. A34030 strain (deposited under the deposit number of FERM BP-10505) at a temperature of 25° C. to 30° C. for 3 days to 12 days in a culture medium comprising the known carbon source, a nitrogen source and an inorganic salt under aerobic conditions to produce and accumulate bispolide A1, bispolide A2 and bispolide A3 having the formula (I) as defined in claim 2, as well as bispolide B1, bispolide B2a, bispolide B2b and bispolide B3 having the formula (II):

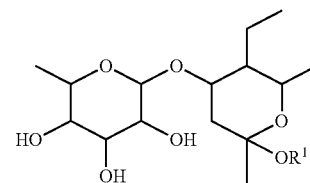
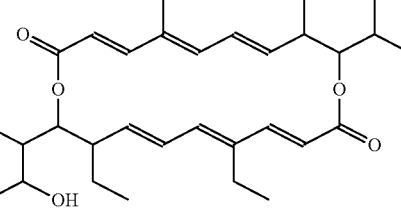
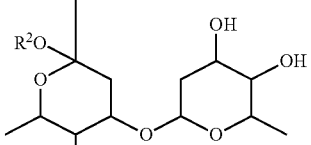

wherein $R^1$ and $R^2$ each denote a hydrogen atom or methyl group (—$CH_3$), and wherein $R^1$ and $R^2$ are each a hydrogen atom for bispolide B1; $R^1$ is a hydrogen atom and $R^2$ is a methyl group for bispolide B2a; $R^1$ is methyl group and $R^2$ is a hydrogen atom for bispolide B2b; and $R^1$ and $R^2$ are each a methyl group for bispolide B3, in the resulting culture, and then recovering at least one of bispolide A1, bispolide A2 and bispolide A3 as well as at least one of bispolide B1, bispolide B2a, bispolide B2b and bispolide B3, whereby at least one of bispolides A1, A2 and A3 and at least one of bispolide B1, B2a, B2b and B3 are harvested from said culture.

13. A pharmaceutical composition comprising as an active ingredient, at least one of bispolide A1, bispolide A2 and bispolide A3 having the formula (I) as defined in claim 2, as well as bispolide B1, bispolide B2a, bispolide B2b and bispolide B3 having the general formula (II):

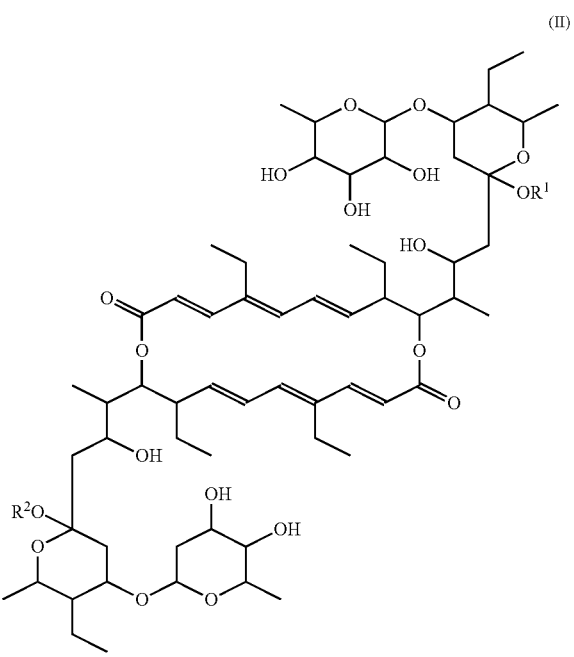

wherein $R^1$ and $R^2$ each denote a hydrogen atom or methyl group (—$CH_3$), and wherein $R^1$ and $R^2$ are each a hydrogen atom for bispolide B1; $R^1$ is a hydrogen atom and $R^2$ is a methyl group for bispolide B2a; $R^1$ is methyl group and $R^2$ is a hydrogen atom for bispolide B2b; and $R^1$ and $R^2$ are each a methyl group for bispolide B3, in admixture with a pharmaceutically acceptable carrier or carriers.

14. The pharmaceutical composition of claim 13, which is an antibacterial composition.

\* \* \* \* \*